United States Patent

Arai et al.

[11] Patent Number: 5,827,799
[45] Date of Patent: Oct. 27, 1998

[54] COMPOUNDS AND HERBICIDES CONTAINING SAME AS ACTIVE COMPONENTS

[75] Inventors: Kiyoshi Arai, Chiba-ken; Fumiaki Koizumi, Fukuoka-ken; Hiroyuki Suzuki, Chiba-ken; Takeshi Kakimoto, Chiba-ken; Sadafumi Koda, Chiba-ken, all of Japan

[73] Assignee: Mitsui Chemicals, Inc., Tokyo, Japan

[21] Appl. No.: 684,231

[22] Filed: Jul. 19, 1996

[30] Foreign Application Priority Data

Jul. 28, 1995 [JP] Japan .................................. 7-192784

[51] Int. Cl.⁶ ..................... C07D 491/00; C07D 495/00; C07D 333/74; C07D 333/76
[52] U.S. Cl. ................. 504/245; 504/289; 504/297; 504/284; 504/271; 504/269; 504/281; 504/282; 504/266; 504/270; 504/276; 546/90; 548/430; 548/431; 548/242; 548/207; 548/209; 548/359.5; 548/151; 548/221; 548/217; 548/302.1
[58] Field of Search ............... 549/44, 45, 47, 549/48, 387; 504/289, 297, 284, 245, 271, 269, 281, 282, 266, 270, 276; 548/430, 431, 242, 207, 209, 359.5, 151, 221, 217, 302.1; 546/90

[56] References Cited

U.S. PATENT DOCUMENTS

| 4,534,785 | 8/1985 | Loh ............................................. 71/88 |
| 5,356,866 | 10/1994 | Arai et al. ................................. 504/292 |
| 5,530,146 | 6/1996 | Arai et al. ................................. 549/476 |

FOREIGN PATENT DOCUMENTS

| 0572001 | 12/1993 | European Pat. Off. . |
| 7-138260 | 5/1995 | Japan . |

OTHER PUBLICATIONS

Database WPI, Week 9531, Derwent Publications Ltd., London, GB; AN 95–234257, XP002016397 & JP–A–07138260 (Mitsui Toatsu Chem., Inc.), May 30, 1995 *Abstract*.

Database WPI, Week 9538, Derwent Publications Ltd., London, GB; AN 95290407, XP002016398 & JP–A–07188244 (Mitsui Toatsu Chem., Inc.), Jul. 25, 1995 *Abstract*.

J. Org. Chem., "Synthesis of Bis–γ–lactones from Diacetone Glucose. 5. Optically Active Canadesolide", Robert Anderson et al, vol. 50, pp. 4786–4790, 1985.

Chemistry and Industry, "Communications to the Editor – An Improved Preparation of 1,2,3,5,–tetra–o–acetyl–β–D–ribofuranose", R.D. Guthrie et al, vol. 27, pp. 547–548, 1968.

Primary Examiner—Mukund J. Shah
Assistant Examiner—Bruck Kifle
Attorney, Agent, or Firm—Burns, Doane, Swecker & Mathis, L.L.P.

[57] ABSTRACT

An object of the invention is to provide herbicides which are completely selective to crops such as paddy rice, soybeans and cotton and have an excellent herbicidal activity on weeds.

The invention relates to ether compounds of the general formula (I)

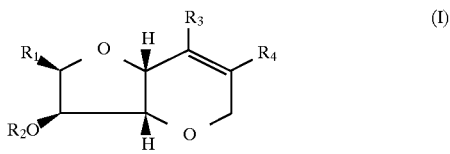

in which $R_1$, $R_2$, $R_3$ and $R_4$ have the same meanings as defined in the text and herbicides containing said compounds as active components.

5 Claims, No Drawings

COMPOUNDS AND HERBICIDES CONTAINING SAME AS ACTIVE COMPONENTS

BACKGROUND OF THE INVENTION

1. Field of the Invention

The present invention relates to ether compounds and herbicides containing these compounds as active components.

2. Description of Prior Art

Compounds of the general formula (1) of the present invention, in which $R_3$ and $R_4$ together form a benzene ring, are described in Japanese Patent Laid-open No. 316579/1994 and No.138260/1995 as having herbicidal activity.

Namely, the Japanese Patent Laid-open No.316579/1994 describes that furobenzopyran derivatives of the general formula (XII)

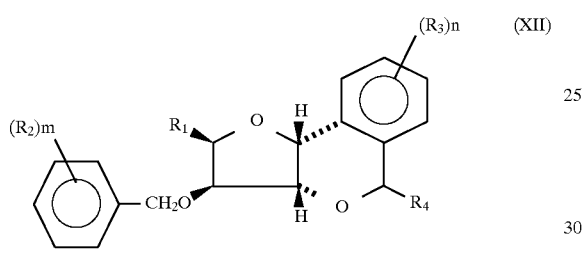

in which $R_1$ is a lower alkyl group, $R_2$ is a lower alkyl group, lower alkoxy group, halogen atom or lower alkyl group substituted by a halogen atom, $R_3$ is a lower alkyl group, lower alkoxy group, halogen atom, lower alkyl group substituted by a halogen atom, phenoxy group or benzyloxy group, $R_4$ is a hydrogen atom or lower alkyl group, m and n are any integers between 0 and 4 and each $R_2$ and $R_3$ may be the same or different when n is 2–4 have herbicidal activity.

Further, the Japanese Patent Laid-open No. 138260/1995 describes that compounds of the general formula (XIII)

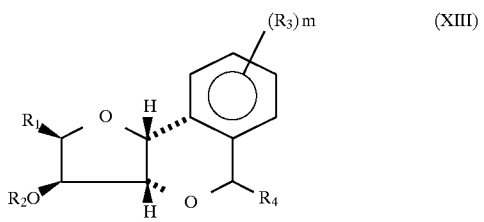

in which $R_1$ is a lower alkyl group, $R_2$ is a lower alkenyl group, lower alkynyl group, methyl group substituted by a cycloalkyl group having 3–7 carbon atoms or a group of one of the general formulae (II)–(XI)

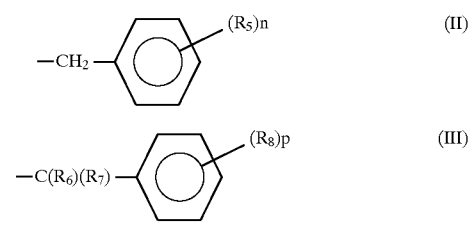

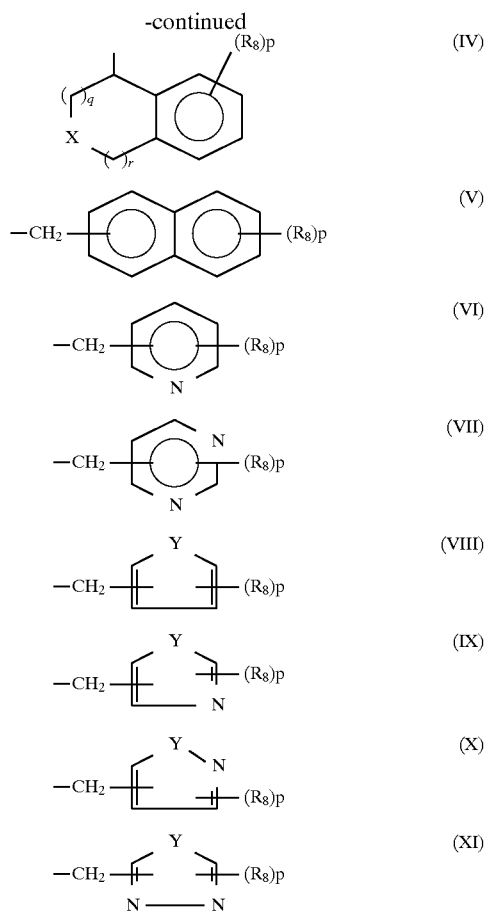

(in which $R_5$ is a hydroxy group, cyano group, lower alkoxy group substituted by a halogen atom, lower alkylthio group, lower alkenyl group or lower alkynyl group, $R_6$ is a hydrogen atom or lower alkyl group, $R_7$ is a lower alkyl group, $R_8$ is a lower alkyl group, lower alkoxy group, halogen atom or lower alkyl group substituted by a halogen atom, X is a methylene group, oxygen atom, sulfur atom or nitrogen atom (which may be substituted by a lower alkyl group or lower acyl group), or may form a double bond with an adjacent carbon atom, Y is an oxygen atom or sulfur atom, n is any integer between 1 and 4 and p is any integer between 0 and 3, each $R_5$ and $R_8$ may be the same or different when n and p are 2 or more, q is 0 or 1, r is any integer between 0 and 2, the sum of q and r is 0, 1 or 2 and X is a methylene group when both r and q are 0).

$R_3$ is a lower alkyl group, lower alkoxy group, halogen atom, lower alkyl group substituted by a halogen atom, phenoxy group, benzyloxy group, cyano group, nitro group, phenyl group, —S(O)$_r$R$_9$ group, —OSO$_2$R$_9$ group, —ZC(=O)R$_9$ group, —ZR$_{10}$ group, —ZCH(R$_{12}$)C(=O)R$_{11}$ group, —ZP(=Z)(ZR$_9$)$_2$ group, —N(R$_{12}$)R$_{13}$ group, —N(R$_{12}$)C(=Z)R$_{14}$ group, —N(R$_{12}$)SO$_2$R$_9$ group, —C(R$_{12}$)$_2$OR$_{13}$ group, —CH(R$_{12}$)S(O)$_r$R$_9$ group, —CH(R$_{12}$)ZC(=O)R$_{14}$ group, —CH(R$_{12}$)N(R$_{12}$)R$_{13}$ group, —CH(R$_{12}$)N(R$_{12}$)C(=Z)R$_{14}$ group, —CH(R$_{12}$)ZP(=Z)(ZR$_9$)$_2$ group, —C(=Z)R$_{11}$ group, —CH(ZR$_{15}$)ZR$_{16}$ group, —C(=Z)N(R$_{17}$)R$_{18}$ group, —CH=NR$_{11}$ group, —CH=CR$_{19}$R$_{20}$ group or —OC(R$_{13}$)$_2$—O—group (in which adjacent carbon atoms on a benzene ring are bound to form a 5-membered ring) (in which R$_9$ is a lower alkyl group or phenyl group (which may be substituted by a lower alkyl group, lower alkoxy group or halogen atom), R$_{10}$ is a lower alkyl group substituted with a halogen atom or alkoxyalkyl group, $R_{11}$ is a hydrogen atom, hydroxy group, lower alkyl group, lower alkoxy group, lower alkylthio group or phenoxy group, $R_{12}$ is a hydrogen atom or lower alkyl group, $R_{13}$ is a hydrogen atom, lower alkyl group, lower alkyl group substituted by a halogen atom or aralkyl group, $R_{14}$ is a lower alkyl group, alkyl group substituted by a halogen atom, phenyl group (which may be substituted by a lower alkyl group, lower alkoxy group or halogen atom) or lower alkoxy group, phenoxy group, lower alkylamino group or anilino group, $R_{15}$ and $R_{16}$ are each independently a hydrogen atom or lower alkyl group or $R_{15}$ and $R_{16}$ are together —(CH$_2$)$_2$— or —(CH$_2$)$_3$— to form a ring, $R_{17}$ is a hydrogen atom or lower alkoxy group, $R_{18}$ is a hydrogen atom, lower alkyl group, phenyl group (which may be substituted by a lower alkyl group, lower alkoxy group or halogen atom) or $R_{17}$ and $R_{18}$ together form a five- or six-membered ring ( in which an oxygen atom, sulfur atom or nitrogen atom may be contained), $R_{19}$ is a hydrogen atom, cyano group or lower alkoxycarbonyl group, $R_{20}$ is a hydrogen atom, lower alkyl group, nitro group, cyano group or lower alkoxycarbonyl group, Z is a hydrogen atom or sulfur atom and t is any integer between 0 and 2) $R_4$ is a hydrogen atom or lower alkyl group, m is any integer between 0 and 4 and each $R_3$ may be the same or different when m is 2 or more have herbicidal activity.

SUMMARY OF THE INVENTION

To date, a number of herbicides for use in upland fields and rice paddies have been developed, but none of these is satisfactory in terms of herbicidal activity or herbicidal selectivity in crop farming. Furobenzopyran derivatives described in Japanese Patent Laid-open No. 316579/1994 and Japanese Patent Laid-open No. 138260/1995 were also not always satisfactory in terms of herbicidal selectivity under conditions where seepage is excessive. Accordingly, an object of the present invention is to find effective compounds which do not damage cultivated crops under any conditions but selectively exhibit herbicidal activity when used in upland field as well as rice paddies.

Thus, one aspect of the present invention is to find compounds having excellent potential as herbicides for use in rice paddies, which are sufficiently selective to paddies rice but exhibit a high herbicidal activity on annual weeds such as *Echinochloa sp., Cyperus diffornis L, Monochoria vaginalis* and *Rotala indica* and perennial weeds such as *Scirpus juncoides, Cyperus serotinus, Eloecharis kuroguwai* and *Eloecharis acicularis*.

Further, another aspect of the present invention is to find compounds which are effective not only as herbicides in rice paddies but also as herbicides in upland fields as well as in other non-agricultural fields by soil application or by foliar application, and thus effective on *Digitaria adscendeus, Stellaria media,* Persicaria, *Amaranthus retroflexus, Cyperus iria, Poltulaca oleracea, Senecio vulgaris, Chenopodium album, Cyperus rotundus, Calystegia japonica, Sagina japonica, Galium aparine, Alopecurus aegualis, Poa annua, Capsella bursa pastoris, Setaria viridis*, etc.

In order to achieve the above-mentioned objectives, the present inventors synthesized a number of novel ether compounds and studied their herbicidal activity in various ways. As a result, the present inventors have found compounds which are effective not only as herbicides in rice paddies but also as herbicides in upland fields as well as in other non-agricultural fields, thereby having completed the present invention.

Namely, the present invention relates to ether compounds of the general formula (I)

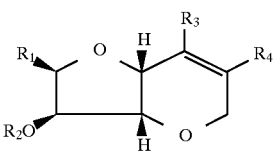

in which $R_1$ is lower alkyl group and $R_2$ is a group selected from general formulae (II) to (XI)

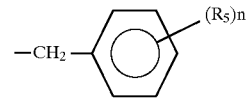

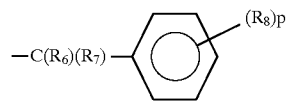

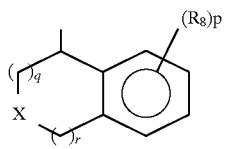

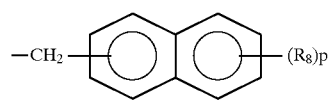

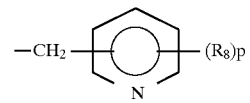

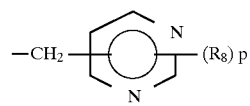

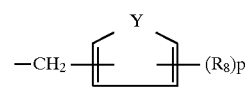

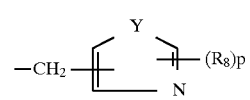

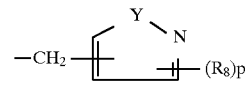

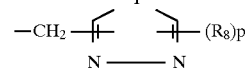

(in which $R_5$ is a lower alkyl group, lower alkoxy group, lower acyloxy group, halogen atom, lower alkyl group substituted by a halogen atom, lower alkoxy group substituted by a halogen atom or lower alkylthio group, $R_6$ is a hydrogen atom or lower alkyl group, $R_7$ is a lower alkyl group, $R_8$ is a lower alkyl group, lower alkoxy group, lower acyloxy group, lower alkylthio group, halogen atom, lower alkyl group substituted by a halogen atom or lower alkoxy group substituted by a halogen atom, X is a methylene group, oxygen atom, sulfur atom or nitrogen atom (which may be substituted by a lower alkyl group or lower acyl group) or may form a double bond with an adjacent carbon atom, Y is an oxygen atom, sulfur atom or nitrogen atom (which may be substituted by a lower alkyl group or lower acyl group), n is any integer between 0 and 5, p is any integer between 0 and 3, each $R_5$ and $R_8$ may be the same or different when n and p are 2 or more, q is 0 or 1, r is any integer between 0 and 2, the sum of q and r is 0, 1 or 2 and X is a methylene group when both r and q are 0), $R_3$ and $R_4$ together form an unsaturated five- or six-membered ring containing 1 or 2 heteroatoms (which may be substituted by a lower alkyl group, lower alkoxy group, lower acyloxy group, lower alkylthio group, halogen atom, lower alkyl group substituted by a halogen atom or lower alkoxy group substituted by a halogen atom) and herbicidal agents which comprise said compounds as effective components.

DETAILED DESCRIPTION AND THE PREFERRED EMBODIMENTS

In the compounds of the present invention, a lower alkyl group, lower alkoxy group, lower acyl group, lower acyloxy group or lower alkylthio group denotes an alkyl group having 1–4 carbon atoms, an alkoxy group having 1–4 carbon atoms, an acyl group having 1–4 carbon atoms, acyloxy group having 1–4 carbon atoms or an alkylthio group having 1–4 carbon atoms, a halogen atom denotes F, Cl, Br or I and a hetero atom denotes an oxygen atom, sulfur atom or nitrogen atom (which may be substituted by a lower alkyl group or lower acyloxy group).

The compounds of the present invention include compounds of the following general formulae

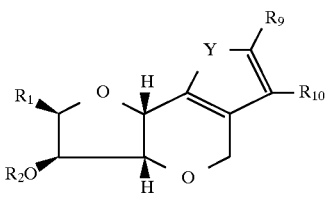
(A-1)

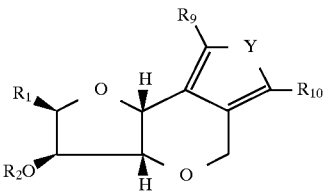
(A-2)

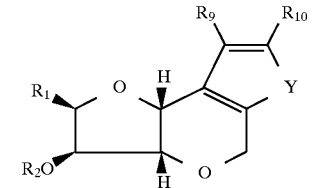
(A-3)

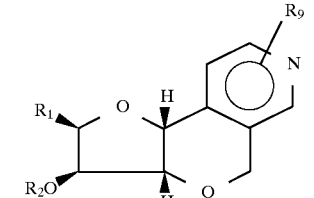
(A-4)

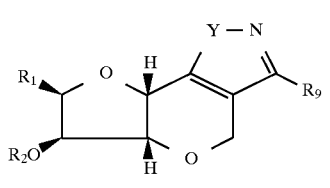
(A-5)

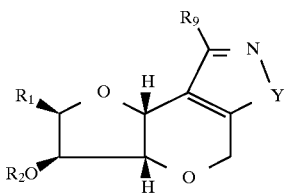
(A-6)

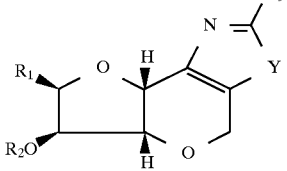
(A-7)

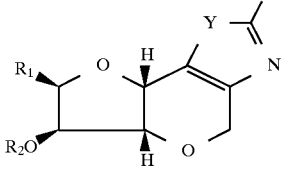
(A-8)

in which $R_9$ and $R_{10}$ are independently a hydrogen atom, alkyl group having 1–4 carbon atoms, alkoxy group having 1–4 carbon atoms or halogen atom, Y is an oxygen atom, sulfur atom or =$NCH_3$.

The compounds of the general formula (I) according to the present invention are novel compounds and are produced by an intramolecular cyclization of tetrahydrofuran derivatives of the general formula (XIV), in which the reaction takes place as shown in the following reaction formulae (1):

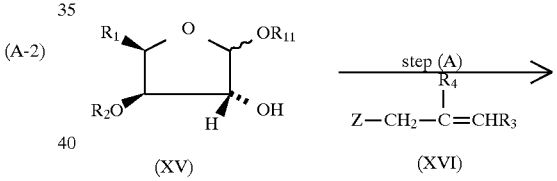

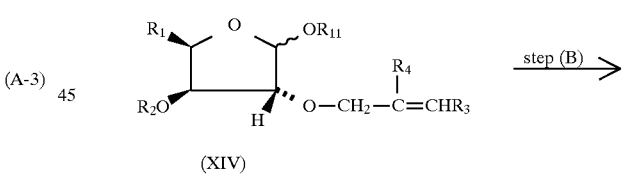

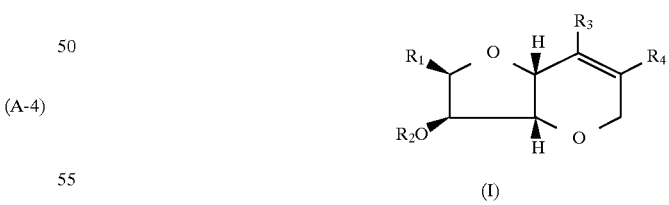
(I)

(Z represents a reactive residue such as a halogen atom and an ester residue.)

in which $R_1$, $R_2$, $R_3$ and $R_4$ have above-mentioned meanings and $R_{11}$ represents a lower alkyl group or lower acyl group.

A method of producing compounds of the present invention (I) is described in detail as follows:

Of the compounds of the general formula (XV), known compounds can be easily synthesized according to the methods described in J. Org. Chem., 50, 4786 (1985) and U.S. Pat. No. 4,534,785. Novel compounds are also included in the compounds of the general formula (XV) and they can be synthesized according to the above-mentioned methods. In general, these compounds are obtained as a mixture of α and β forms; the mixture can be separated into isomers, for example by silica gel chromatography, and the isomers can be used for the subsequent reaction.

In the reaction formulae (1), the compounds of the general formula (XIV) can be obtained via step (A) by reacting a compound of the general formula (XV) with an equivalent or slightly excess amount of a compound of the general formula (XVI) in an inert solvent such as n-hexane, benzene, toluene, xylene, diethyl ether, dioxane, tetrahydrofuran, dimethylformamide, dimethyl sulfoxide, chlorobenzene, methylene chloride, chloroform, methyl ethyl ketone, acetone or acetonitrile, in the presence of an inorganic base such as potassium carbonate, sodium carbonate, sodium hydroxide, potassium hydroxide, sodium hydride or sodium amide or silver oxide (I). Alternatively, it is possible to carry out the reaction in a two-phase system of an organic solvent such as benzene or toluene and water in the presence of a phase-transfer catalyst such as a quaternary ammonium salt or phosphate. The reaction temperature can be between −30° C. and the boiling point of the solvent but a temperature between room temperature and 60° C. is advantageous. After the reaction, the resultant product is treated in a conventional manner and the target compound can be purified by recrystallization or column chromatography. Further, compounds of the general formula (XIV), in which $R_{11}$ is an acyl group, can be easily synthesized from compounds of the general formula(XIV), in which $R_{11}$ is an alkyl group, by a generally known method (e.g., Chem. Ind., 27, 547, (1968)).

The compounds of the general formula (I) according to the present invention can be obtained via step (B) by an intramolecular cyclization reaction of the compounds of the general formula (XIV) in an inert solvent such as n-hexane, nitrobenzene, chlorobenzene, methylene chloride, chloroform, carbon tetrachloride, 1,2-dichloroethane, carbon disulfide or acetonitrile in the presence of a Lewis acid such as tin tetrachloride, titanium tetrachloride, aluminum chloride, iron (III) chloride or boron trifluoride-diethyl ether complex or inorganic or organic acid such as sulfuric acid, nitric acid, hydrochloric acid, chlorosulfonic acid, phosphoric acid, benzenesulfonic acid, trifluoroacetic acid or trifluoromethanesulfonic acid. The reaction temperature can be between −70° C. and the boiling point of the solvent used, but a temperature in a lower range is advantageous for the reaction and thus a preferable temperature is between −70° and 30° C. After the reaction, the resultant product is treated in a conventional manner and the target compound can be purified by recrystallization or column chromatography.

The compounds of the present invention are markedly harmless to crops as compared with other compounds under conditions with water seeping that often cause damages by chemicals. Namely, the compounds of the general formula (I) of the present invention have excellent potential as herbicides for use in rice paddies, which are sufficiently harmless to the paddy rice but exhibit a high herbicidal activity on annual weeds such as *Echinochloa sp., Cyperus diffornis* L, *Monochoria vaginalis* and *Rotala indica* and perennial weeds such as *Scirpus juncoides, Cyperus serotinus, Eloecharis kuroguwai* and *Eloecharis acicularis*. Further, these compounds are effective not only as herbicides in rice paddies but also as herbicides in upland fields by soil application or by foliar application, and present sufficient selectivity to crops such as soy beans, cotton, sugar beats, corn, sugar cane, barley, wheat, oats and rye and a herbicidal effect on *Digitaria adscendeus, Stellaria media, Persicaria, Amaranthus retroflexus, Cyperus iria, Poltulaca oleracea, Senecio vulgaris, Chenopodium album, Cyperus rotundus, Calystegia japonica, Sagina japonica, Galium aparine, Alopecurusa aequalis, Poa annua, Capsella bursa pastoris, Setaria viridis*, etc.

The compounds (I) of the present invention may be applied in their pure forms onto plants to be treated; however, in general, they are mixed with inert liquid carrier or solid carriers and used in the forms of conventional formulations such as powders, granules, wettable powders, emulsions and flowable formulations. If necessary, auxiliary agents can be added to ease the formulation.

As to carriers, there is no restriction and any solid or liquid carrier which is customarily used for agricultural and horticultural formulations can be used. Examples of the solid carriers include mineral powders such as clay, talc, bentonite, calcium carbonate, diatomaceous earth and white carbon, plant powders such as soybean powder and starch, polymers such as petroleum resins, polyvinyl alcohol and polyalkylene glycols, urea and waxes. Examples of liquid carriers include various oils, various organic solvents and water.

As to auxiliary agents, surfactants, binders, stabilizers or the like, which are customarily used in agricultural and horticultural formulations, can be used alone or in combination if appropriate. In some cases, bactericidal or fungicidal agents for industrial use can be added.

As to surfactants, nonionic, anionic, cationic or amphoteric surfactant are conveniently used. Preferable examples are alkylphenols, higher alcohols, alkylnaphthols, higher fatty acids, fatty acid esters, polymers in which ethylene oxide and propylene oxide are polymerized with dialkylphosphoric amine or the like, alkylsulfuric ester salts (e.g., sodium lauryl sulfate), alkyl sulfonates (e.g., sodium 2-ethylhexenesulfonate), and aryl sulfonates (e.g., lignin sodium sulfonate and sodium dodecylbenzenesulfonate).

The concentration of the compounds of the general formula (I) in herbicides according to the present invention varies depending on the forms of the formulations; in general, 1–20% by weight in powders, 20–60% by weight in wettable powders, 1–30% by weight in granules, 1–50% by weight in emulsions, 10–50% by weight in flowable formulations and 20–90% by weight in dry flowable formulations. The concentration of auxiliary agents is 0–80% by weight, and the concentration of carriers is calculated by subtracting the amount of active ingredients and auxiliary agents from the total, i.e., 100% by weight.

The herbicides according to the present invention are effective for any treatment methods such as a flooding soil treatment, ordinary soil treatment, mixing-phase soil treatment, and spraying for stalks and leaves. The appropriate amount for applications varies widely between 0.01 kg and 10 kg/ha of an active ingredient; a standard application preferably ranges between 0.05 and 5 kg/ha.

The herbicides according to the present invention can be used in combination with one or more other herbicides, agricultural chemicals such as insecticides and plant growth regulators, soil improvers or fertilizers and can be combined to formulate mixed formulations, thereby occasionally exerting synergistic effects. In this connection, it is particularly advantageous to use the herbicides of the present invention as mixtures with other herbicides.

Examples of other herbicides include phenoxyacetic acid herbicides, benzoic acid herbicides, chlorinated carboxylic acid herbicides, carbamate herbicides, urea herbicides, sulfonylurea herbicides, acid amide herbicides, heterocyclic herbicides (e.g., triazine herbicides and diazine herbicides), phenol herbicides, diphenyl ether herbicides, dipyridinium herbicides, dinitroaniline herbicides, organic phosphoric ester herbicides, phosphor-containing amino acid herbicides, imidazolidinone herbicides, pyridine herbicides, quinoline herbicides, sulfonamide herbicides, cyclohexanone herbicides, other organic herbicides and inorganic herbicides.

EXAMPLES

The present invention will be explained in more detail by the following Examples.

First, the process for producing the compounds of the general formula (XIV) and (XV) is given as Reference Examples.

Reference Example 1

Preparation of methyl 5-deoxy-5-C-methyl-3-O-(2-methylbenzyl)-D-xylofuranoside:

67.97 g of 5-deoxy-1,2-O-isopropylidene-5-C-methyl-3-O-(2-methylbenzyl)-α-D-xylofuranose were dissolved in methanol (300 ml) and then 0.5 g of p-toluenesulfonic acid was added therein and the mixture was refluxed for 10 hours while heating. After cooling in air, the reaction solution was neutralized with an aqueous sodium hydrogen carbonate solution and then the solvent was evaporated under reduced pressure. The resultant substance was added to water and extracted with an ether/ethyl acetate (1:1) mixed solvent. The organic phase was washed with water and then dried with anhydrous sodium sulfate. The solvent was evaporated under reduced pressure to obtain an oily crude product. The crude product was purified by silica gel chromatography (developing solvent: n-hexane:ethyl acetate=3:1) and 60.8 g of the target compound were obtained as an anomeric mixture of α and β forms. (Yield: 98.2%)

Reference Example 2

Preparation of methyl 5-deoxy-3-O-(2-fluorobenzyl)-5-C-methyl-D-xylofuranoside:

10.68 g of 5-deoxy-3-O-(2-fluorobenzyl)-1,2-O-isopropylidene-5-C-methyl-α-D-xylofuranose were dissolved in methanol (100 ml) and then 0.5 g of p-toluenesulfonic acid was added therein and the mixture was refluxed for 10 hours while heating. After cooling in air, the reaction mixture was treated in the same manner as described in Reference Example 1 and 9.31 g of the target compound were obtained as an anomeric mixture of α and β forms.

(Yield: 95.6%)

Reference Example 3

Preparation of methyl 5-deoxy-5-C-methyl-3-O-(thiophene-3-yl-methyl)-D-xylofuranoside:

38.70 g of 5-deoxy-1,2-O-isopropylidene-5-C-methyl-3-O-(thiophene-3-yl-methyl)-α-D-xylofuranose were dissolved in methanol (200) and then 0.4 g of p-toluenesulfonic acid was added therein and the mixture was refluxed for 10 hours while heating. After cooling in air, the reaction mixture was treated in the same manner as described in Reference Example 1 and 34.7 g of the target compound were obtained as an anomeric mixture of α and β forms. (Yield: 98.7%)

Reference Example 4

Preparation of methyl 5-deoxy-5-C-methyl-3-O-(2-methylbenzyl)-2-O-(thiophene-3-yl-methyl)-D-xylofuranoside:

10.0 g of methyl 5-deoxy-5-C-methyl-3-O-(2-methylbenzyl)-D-xylofuranoside obtained in Reference Example 1 were dissolved in 50 ml of tetrahydrofuran and then 2.1 g of oily sodium hydride (containing 40% liquid paraffin) were gradually added therein while stirring. 0.4 g of tetrabutylammonium iodide and 8.6 g of 3-bromomethylthiophene were added therein and the mixture was refluxed for 5 hours while heating. After cooling in ice and adding a small amount of water, the solvent was evaporated under reduced pressure and the resultant crude product was added to water and extracted with ether. The organic phase was thoroughly washed with water and then dried with anhydrous sodium sulfate. The solvent was evaporated under reduced pressure to obtain an oily crude product. The crude product was purified by silica gel chromatography (developing solvent: n-hexane:ethyl acetate= 10:1) and 11.77 g of the target compound were obtained as an anomeric mixture of α and β forms. (Yield: 86.5%)

The anomeric mixture of α and β forms thus obtained was further purified by silica gel chromatography (developing solvent: n-hexane:ethyl acetate=12:1) and separated into α form and β form fractions.

$^1$H-NMR(CDCl$_3$, 270 MHz) δ ppm; α-anomer; 0.94 (3H, t, J=7.3 Hz), 1.61 (2H, dq, J=7.3, 7.3 Hz), 2.29 (3H, s), 3.40 (3H, s), 3.95–4.14 (3H, m), 4.45 (1H, d, J=11.7 Hz), 4.57 (1H, d, J=12.5 Hz), 4.61 (1H, d, J=11.7 Hz), 4.67 (1H, d, J=12.5 Hz), 4.79 (1H, d, J=4.4 Hz), 7.10–7.32 (7H, m) β-anomer; 0.94 (3H, t, J=7.3 Hz), 1.68 (2H, dq, J=7.3, 7.3 Hz), 2.31 (3H, s), 3.41 (3H, s), 3.91–4.09 (3H, m), 4.44 (1H, d, J=11.7 Hz), 4.53 (1H, d, J=11.7 Hz), 4.59 (1H, d, J=11.7 Hz), 4.61 (1H, d, J=11.7 Hz), 4.84 (1H, d, J=2.2 Hz), 7.05–7.33 (7H, m)

Reference Example 5

Preparation of methyl 5-deoxy-3-O-(2-fluorobenzyl)-5-C-methyl-2-O-(thiophene-2-yl-methyl)-D-xylofuranoside:

14.7 g of methyl 5-deoxy-3-O-(2-fluorobenzyl)-5-C-methyl-D-xylofuranoside obtained in Reference Example 2 were dissolved in 150 ml of tetrahydrofuran and then 3.1 g of oily sodium hydride (containing 40% liquid paraffin) were gradually added therein while stirring. 0.6 g of tetrabutylammonium iodide and 9.4 g of 2-chloromethylthiophene were added therein and the mixture was refluxed for 4 hours while heating. After cooling in air, the reaction mixture was treated in the same manner as described in Reference Example 4 and 16.42 g of the target compound were obtained as an anomeric mixture of α and β forms.

(Yield: 82.4%)

$^1$H-NMR(CDCl$_3$, 270 MHz) δ ppm; 0.94 (3H, t, J=7.3 Hz), 1.68 (2H, dq, J=7.3, 7.3 Hz), 3.41 (3H, s), 3.92–3.95 (1H, m), 4.02–4.06 (2H, m), 4.41–4.48 (1H, m), 4.58–4.73 (3H, m), 4.82–4.86 (1H, m), 6.91–7.01 (2H, m), 7.14–7.32 (51, m).

Reference Example 6

Preparation of methyl 5-deoxy-5-C-methyl-2-O-(thiophene-3-yl-methyl)-3-O-(thiophene-3-yl-methyl)-D-xylofuranoside:

15.20 g of methyl 5-deoxy-5-C-methyl-3-O-(thiophene-3-yl-methyl)-D-xylofuranoside obtained in Reference Example 3 were dissolved in 200 ml of tetrahydrofuran and then 4.69 g of oily sodium hydride (containing 40% liquid paraffin) were gradually added therein while stirring. 0.80 g of tetrabutylammonium iodide and 10.14 g of 3-chloromethylthiophene were added therein and the mixture was refluxed for 4 hours while heating. After cooling in air, the reaction mixture was treated in the same manner as described in Reference Example 4 and 18.67 g of the target compound were obtained as an anomeric mixture of α and β forms. (Yield: 89.5%)

¹H-NMR(CDCl₃, 270 MHz) δ ppm; 0.92 (3H, t, J=7.3 Hz), 1.67 (2H, dq, J=7.3, 7.3 Hz), 3.40 (3H, s), 3.90–4.10 (3H, m), 4.53–4.62 (4H, m), 4.78–4.80 (1H, m), 6.75–6.80 (2H, m), 6.92–7.00 (2H, m), 7.05–7.20 (2H, m)

Reference Example 7

Preparation of methyl 5-deoxy-2-O-(furan-2-yl-methyl)-5-C-methyl-3-O-(2-methylbenzyl)-D-xylofuranoside:

18.8 g of methyl 5-deoxy-5-C-methyl-3-O-(2-methylbenzyl)-D-xylofuranoside obtained in Reference Example 1 were dissolved in 200 ml of tetrahydrofuran and then 3.95 g of oily sodium hydride (containing 40% liquid paraffin) were gradually added therein while stirring. 0.78 g of tetrabutylammonium iodide and 10.7 g of 2-chloromethylfuran were added therein and the mixture was refluxed for 5 hours while heating. After cooling in air, the reaction mixture was treated in the same manner as described in Reference Example 4 and 19.68 g of the target compound were obtained as an anomeric mixture of α and β forms. (Yield: 80.5%).

¹H-NMR(CDCl₃, 270 MHz) δ ppm; 0.94 (3H, t, J=7.3 Hz), 1.68 (2H, dq, J=7.3, 7.3 Hz), 2.29 (3H, s), 3.40 (3H, s), 3.90–4.08 (3H, m), 4.52–4.67 (4H, m), 4.79–4.82 (1H, m), 6.35 (2H, d, J=1.5 Hz), 6.99–7.15 (2H, m), 7.23–7.29 (1H, m), 7.38–7.44 (2H, m) Reference Example 8

Preparation of methyl 5-deoxy-2-O-(furan-3-yl-methyl)-5-C-methyl-3-O-(2-methylbenzyl)-D-xylofuranoside:

2.1 g of methyl 5-deoxy-5-C-methyl-3-O-(2-methylbenzyl)-D-xylofuranoside obtained in Reference Example 1 were dissolved in 10 ml of tetrahydrofuran and then 0.44 g of oily sodium hydride (containing 40% liquid paraffin) was gradually added therein while stirring. 0.08 g of tetrabutylammonium iodide and 2.8 g of 3-chloromethylfuran were added therein and the mixture was refluxed for 4 hours while heating. After cooling in air, the reaction mixture was treated in the same manner as described in Reference Example 4 and 2.14 g of the target compound were obtained as an anomeric mixture of α and β forms. (Yield: 78%)

The anomeric mixture of α and β forms thus obtained was further purified by silica gel chromatography (developing solvent: n-hexane:ethyl acetate=15:1) and separated into α form and β form fractions.

1H-NMR(CDCl₃, 270 MHz) δ ppm; α-anomer; 0.94 (3H, t, J=7.3 Hz), 1.56–1.69 (2H, m), 2.29 (3H, s), 3.41 (3H, s), 3.95–3.99 (1H, m), 4.07–4.13 (2H, m), 4.44 (1H, d, J=11.7 Hz), 4.46 (1H, d, J=11.7 Hz), 4.54 (1H, d, J=11.7 Hz), 4.62 (1H, d, J=11.7 Hz), 4.83 (1H, d, J=4.4 Hz), 7.13–7.41 (6H, m); β-anomer; 0.94 (3H, t, J=7.31 Hz), 1.68 (2H, dq, J=7.3, 7.3 Hz), 2.32 (3H, s), 3.41 (3H, s), 3.90–4.08 (3H, m), 4.37–4.47 (3H, m), 4.60 (1H, d, J=12.5 Hz), 4.83 (1H, d, J=2.2 Hz), 6.41 (1H, s), 7.14–7.40 (6H, m)

Reference Example 9

Preparation of methyl 5-deoxy-3-O-(2-fluorobenzyl)-5-C-methyl-2-O-(thiophene-3-yl-methyl)-D-xylofuranoside:

3.27 g of methyl 5-deoxy-3-O-(2-fluorobenzyl)-5-C-methyl-D-xylofuranoside obtained in Reference Example 2 were dissolved in 27 ml of tetrahydrofuran and then 0.58 g of oily sodium hydride (containing 40% liquid paraffin) was gradually added therein while stirring. 0.09 g of tetrabutylammonium iodide and 1.68 g of 3-chloromethylthiophene were added therein and the mixture was refluxed for 7 hours while heating. After cooling in air, the reaction mixture was treated in the same manner as described in Reference Example 4 and 3.61 g of the target compound were obtained as an anomeric mixture of α and β forms. (Yield: 81.4%)

The anomeric mixture of α and β forms thus obtained was further purified by silica gel chromatography (developing solvent: n-hexane:ethyl acetate=15:1) and separated into α form and α form fractions.

¹H-NMR(CDCl₃, 270 MHz) δ ppm; α-anomer; 0.95 (3H, t, J=7.3 Hz), 1.56–1.69 (2H, m), 3.40 (3H, s), 3.96 (1H, t, J=4.4 Hz), V4, 08–4.15 (2H, m), 4.55 (1H, d, J=11.7 Hz), 4.60 (1H, d, J=11.7 Hz), 4.68 (2H, d, J=11.7 Hz), 4.78 (1H, d, J=4.4 Hz), 6.99–7.14 (3H, m), 7.23–7.32 (3H, m), 7.36–7.41 (1H, m); β-anomer; 0.95 (3H, t, J=7.3 Hz), 1.69 (2H, dq, J=7.3, 7.3 Hz), 3.40 (3H, s), 3.92–4.09 (3H, m), 4.53–4.67 (4H, m), 4.84 (1H, d, J=2.2 Hz), 6.99–7.15 (3H, m), 7.22–7.32 (3H, m),7.38–7.44 (1H, m)

Example 1

Preparation of (2R,3S,3aS,8bS)-2-ethyl-3-(2-methylbenzyloxy)-3,3a,5,8b-tetrahydro-2H-thieno-[2,3-d]furo[3,2-b]pyran (compound No. 7 of the general formula (I)):

1.0 g of methyl 5-deoxy-5-C-methyl-3-O-(2-methylbenzyl)-2-O-(thiophene-3-yl-methyl)-D-xylofuranoside (α- and β-form mixture) obtained in Reference Example 4 was dissolved in 10 ml of dichloromethane and then 1.0 g of trifluoroacetic acid was added therein while cooling in ice. The mixture was stirred at room temperature for 3 hours and then poured into an aqueous sodium hydrogencarbonate saturated solution with ice. The organic phase was thoroughly washed with water and dried on anhydrous sodium sulphate. The solvent was evaporated under reduced pressure to obtain an oily crude product. The crude product was purified by silica gel chromatography (developing solvent: n-hexane:ethyl acetate=10:1) and 0.76 g of the target compound was obtained as an oily product. (Yield: 83%)

¹H-NMR(CDCl₃, 270 MHz) δ ppm; 0.87 (3H, t, J=7.3 Hz), 1.75 (2H, dq, J=7.3, 7.3 Hz), 2.36 (3H, s), 4.02 (1H, d, J=2.9 Hz), 4.16–4.23 (1H, m), 4.27 (1H, d, J=2.9 Hz), 4.55 (1H, d, J=11.7 Hz), 4.59 (1H, d J=13.9 Hz), 4.75 (1H, d, J=11.7 Hz), 4.83 (1H, d, J=13.9 Hz), 5.00 (1H, d, J=2.9 Hz), 6.78 (1H, d, J=5.1 Hz), 7.15–7.30 (4H, m), 7.34–7.37 (1H, m) $[\alpha]_D^{25}$=−51.98° (c=0.81, EtOH)

Example 2

Preparation of (2R,3S,3aS,8bR)-2-ethyl-3-(2-fluorobenzyloxy)-3,3a,5,8b-tetrahydro-2H-thieno-[3,2-d]furo[3,2-b]pyran (compound No. 76 of the general formula (I)):

4.0 g of methyl 5-deoxy-3-O-(2-fluorobenzyl)-5-C-methyl-2-O-(thiophene-2-yl-methyl)-D-xylofuranoside (α-and β-form mixture) obtained in Reference Example 5 were dissolved in 20 ml of dichloromethane and then 3.7 g of trifluoroacetic acid were added therein while cooling in ice. The mixture was stirred at room temperature for 3 hours and then poured into an aqueous sodium hydrogencarbonate saturated solution with ice. The organic phase was thoroughly washed with water and dried on anhydrous sodium sulphate. The solvent was evaporated under reduced pressure to obtain an oily crude product. The crude product was purified by silica gel chromatography (developing solvent: n-hexane:ethyl acetate=10:1) and 2.78 g of the target compound were obtained as an oily product. (Yield: 76%)

$^1$H-NMR(CDCl$_3$, 270 MHz) δ ppm; 0.89 (3H, t, J=7.3 Hz), 1.75 (2H, dq, J=7.3, 7.3 Hz), 4.02 (1H, d, J=3.7 Hz), 4.12–4.18 (1H, m), 4.28 (1H, d, J=2.9 Hz), 4.65 (1H, d, J=11.7 Hz), 4.71 (1H, d, J=14.7 Hz), 4.81 (1H, d, J=11.7 Hz), 4.91 (1H, d, J=14.7 Hz), 4.90 (1H, d, J=2.9 Hz), 7.42–7.48 (1H, m), 7.0–7.31 (5H, m), 7.42–7.48 (1H, m)

Example 3

Preparation of (2R,3S,3aS,8bS)-2-ethyl-3-(thiophene-3-yl-methyloxy)-3,3a,5,8b-tetrahydro-2H-thieno-[2,3-d]furo[3,2-b]pyran (compound No. 30 of the general formula (I)):

2.0 g of methyl 5-deoxy-5-C-methyl-2-O-(thiophene-3-yl-methyl)-3-O-(thiophene-3-yl-methyl)-D-xylofuranoside (α- and β-form mixture) obtained in Reference Example 6 were dissolved in 10 ml of 1,2-dichloroethane and then 1.1 g of sulfuric acid was added therein while cooling in ice. The mixture was stirred at room temperature for 3 hours and then poured into an aqueous sodium hydrogencarbonate saturated solution with ice. The organic phase was thoroughly washed with water and dried on anhydrous sodium sulphate. The solvent was evaporated under reduced pressure to obtain an oily crude product. The crude product was purified by silica gel chromatography (developing solvent: n-hexane:ethyl acetate=8:1) and 1.53 g of the target compound were obtained as an oily product. (Yield: 84%)

$^1$H-NMR(CDCl$_3$, 270 MHz) δ ppm; 0.87 (3H, t, J=7.3 Hz), 1.75 (2H, dq, J=7.3, 7.3 Hz), 4.03 (1H, d, J=2.9 Hz), 4.15–4.23 (1H, m), 4.27 (1H, d, J=2.9 Hz), 4.57 (1H, d, J=11.7 Hz), 4.60 (1H, d, J=14.6 Hz), 4.77 (1H, d, J=11.7 Hz), 4.84 (1H, d, J=14.6 Hz), 5.00 (1H, d, J=2.9 Hz), 6.78 (1H, d, J=5.1 Hz), 7.05 (1H, d, J=5.4 Hz), 7.14–7.37 (3H, m)

Example 4

Preparation of (2R,3S,3aS,8bR)-2-ethyl-3-(2-methylbenzyloxy)-3,3a,5,8b-tetrahydro-2H-furo-[2,3-e]furo[2,3-c]pyran (compound No. 78 of the general formula (I)):

2.0 g of methyl 5-deoxy-2-O-(furan-2-yl-methyl)-5-C-methyl-3-O-(2-methylbenzyl)-D-xylofuranoside obtained in Reference Example 7 were dissolved in 10 ml of 1,2-dichloroethane and then 1.54 g of aluminum chloride were added therein while cooling in ice. The mixture was stirred at room temperature for 3 hours and then poured into an aqueous sodium hydrogencarbonate saturated solution with ice. The organic phase was thoroughly washed with water and dried on anhydrous sodium sulphate. The solvent was evaporated under reduced pressure to obtain an oily crude product. The crude product was purified by silica gel chromatography (developing solvent: n-hexane:ethyl acetate=8:1) and 1.1 g of the target compound were obtained as an oily product. (Yield: 62%)

$^1$H-NMR(CDCl$_3$, 270 MHz) δ ppm; 0.88 (3H, t, J=7.3 Hz), 1.75 (2H, dq, J=7.3, 7.3 Hz), 2.35 (3H, s), 4.01 (1H, d, J=3.7 Hz), 4.12–4.20 (1H, m), 4.26 (1H, d, J=2.9 Hz), 4.57 (1H, d, J=11.7 Hz), 4.60 (1H, d, J=15.4 Hz), 4.73 (1H, d, J=11.7 Hz), 4.81 (1H, d, J=15.4 Hz), 4.90 (1H, d, J=2.9 Hz), 6.37 (1H, d, J=1.8 Hz), 7.12–7.42 (5H, m)

Example 5

Preparation of (2R,3S,3aS,8bS)-2-ethyl-3-(2-methylbenzyloxy)-3,3a,5,8b-tetrahydro-2H-furo-[2,3-e]furo[3,2-c]pyran (compound No. 8 of the general formula (I)):

1.46 g of methyl 5-deoxy-2-O-(furan-3-yl-methyl)-5-C-methyl- 3-O-(2-methylbenzyl)-D-xylofuranoside obtained in Reference Example 8 were dissolved in 10 ml of 1,2-dichloroethane and then 1.45 g of trifluoroacetic acid were added therein at room temperature. The mixture was refluxed for 3 hours while heating and then poured into an aqueous sodium hydrogencarbonate saturated solution with ice. The organic phase was thoroughly washed with water and dried on anhydrous sodium sulphate. The solvent was evaporated under reduced pressure to obtain an oily crude product. The crude product was purified by silica gel chromatography (developing solvent: n-hexane:ethyl acetate=10:1) and 1.13 g of the target compound were obtained as an oily product. (Yield: 85%)

$^1$H-NMR(CDCl$_3$, 270 MHz) δ ppm; 0.87 (3H, t, J=7.3 Hz), 1.74 (2H, dq, J=7.3, 7.3 Hz), 2.35 (3H, s), 3.97 (1H, d, J=2.9 Hz), 4.16–4.23 (1H, m), 4.27 (1H, d, J=2.9 Hz), 4.54 (1H, d, J=11.7 Hz), 4.56 (1H, d , J=13.9 Hz), 4.70 (1H, d, J=13.9 Hz), 4.73 (1H, d, J=11.7 Hz), 4.89 (1H, d, J=2.9 Hz), 6.23 (1H, d, J=2.2 Hz), 7.15–7.26 (3H, m), 7.33–7.39 (2H, m) [α]$_D^{25}$ =–40.50° (c=0.80, EtOH)

Example 6

Preparation of (2R,3S,3aS,8bS)-2-ethyl-3-(2-fluorobenzyloxy) -3,3a,5,8b-tetrahydro-2H-thieno-[2,3-d]furo-[3,2-b]pyran (compound No. 3 of the general formula (I)):

1.6 g of methyl 5-deoxy-3-O-(2-fluorobenzyl)-5-C-methyl-2-O-(thiophene-3-yl-methyl)-D-xylofuranoside (α-and β-form mixture) obtained in Reference Example 9 were dissolved in 20 ml of dichloromethane and then 2.1 g of trifluoroacetic acid were added therein while cooling in ice. The mixture was stirred at room temperature for 12 hours and then poured into an aqueous sodium hydrogencarbonate saturated solution with ice. The organic phase was thoroughly washed with water and dried on anhydrous sodium sulphate. The solvent was evaporated under reduced pressure to obtain an oily crude product. The crude product was purified by silica gel chromatography (developing solvent: n-hexane:ethyl acetate=9:1) and 1.35 g of the target compound were obtained as an oily product. (Yield: 92%)

$^1$H-NMR(CDCl$_3$, 270 MHz) δ ppm; 0.90 (3H, t, J=7.3 Hz), 1.75 (2H, dq, J=7.3, 7.3 Hz), 4.04 (1H, d, J=3.7 Hz), 4.20 (1H, dt, J=3.7, 7.3 Hz), 4.29 (1H, d, J=3.7 Hz), 4.60 (1H, d, J=14.7 Hz), 4.64 (1H, d, J=12.5 Hz), 4.81 (1H, d, J=12.5 Hz), 4.83 (1H, d, J=14.7 Hz), 5.00 (1H, d, J=3.7 Hz), 6.78 (1H, d, J=5.1 Hz), 7.02–7.09 (1H, m), 7.12–7.18 (1H, m), 7.26–7.34 (2H, m), 7.42–7.47 (1H, m) [α]$_D^{25}$=–37.85° (c=0.81, EtOH)

Structures of the compounds of the general formula (I) which can be produced in the same manner as described in Examples 1–6 are given in Tables 1–8 as structures (A-l)–(A-8) and their physical properties are given in Table 9.

TABLE 1

Compounds in general formula (A-1)
Substituent in general formula (A-1)

| Compound No. | $R_1$ | $R_2$ general formula | $(R_5)_n$ | Y | $R_9$ | $R_{10}$ |
|---|---|---|---|---|---|---|
| 1 | $C_2H_5$ | (II) | H | O | H | H |
| 2 | $C_2H_5$ | (II) | o-F | O | H | H |
| 3 | $C_2H_5$ | (II) | o-F | S | H | H |
| 4 | $C_2H_5$ | (II) | o-F | S | Cl | H |
| 5 | $C_2H_5$ | (II) | o-$CH_3$ | S | Cl | H |
| 6 | $C_2H_5$ | (II) | o-$CH_3$ | S | Br | H |
| 7 | $C_2H_5$ | (II) | o-$CH_3$ | S | H | H |
| 8 | $C_2H_5$ | (II) | o-$CH_3$ | O | H | H |
| 9 | $CH_3$ | (II) | m-$OCH_3$ | S | Cl | H |
| 10 | $C_2H_5$ | (II) | p-F | O | H | H |
| 11 | $CH_3$ | (II) | p-F | $NCH_3$ | H | H |
| 12 | $C_2H_5$ | (II) | p-Cl | $NCH_3$ | H | H |

| Compound No. | $R_1$ | $R_2$ general formula | $R_6$ | $R_7$ | $(R_8)_p$ | Y | $R_9$ | $R_{10}$ |
|---|---|---|---|---|---|---|---|---|
| 13 | $C_2H_5$ | (III) | H | $CH_3$ | H | O | H | H |
| 14 | $C_2H_5$ | (III) | $CH_3$ | $CH_3$ | H | S | H | H |
| 15 | $C_2H_5$ | (III) | H | $CH_3$ | H | S | Cl | H |

| Compound No. | $R_1$ | $R_2$ general formula | q | r | X | $(R_8)_p$ | Y | $R_9$ | $R_{10}$ |
|---|---|---|---|---|---|---|---|---|---|
| 16 | $CH_3$ | (IV) | 1 | 1 | $CH_2$ | H | O | $CH_3$ | H |
| 17 | $C_2H_5$ | (IV) | 0 | 1 | $CH_2$ | H | O | H | H |
| 18 | $C_2H_5$ | (IV) | 1 | 1 | O | H | S | H | H |
| 19 | $C_2H_5$ | (IV) | 1 | 1 | S | H | S | Cl | H |
| 20 | $C_2H_5$ | (IV) | 1 | 0 | $NCOCH_3$ | H | $NCH_3$ | H | H |

| Compound No. | $R_1$ | $R_2$ general formula | position | $(R_8)_p$ | Y | $R_9$ | $R_{10}$ |
|---|---|---|---|---|---|---|---|
| 21 | $C_2H_5$ | (V) | 1 | 4-Cl | O | H | H |
| 22 | $C_2H_5$ | (V) | 2 | 3-Cl | O | Br | H |
| 23 | $C_2H_5$ | (V) | 2 | H | S | Cl | H |
| 24 | $C_2H_5$ | (VI) | 2 | H | O | H | H |
| 25 | $C_2H_5$ | (VI) | 3 | H | S | I | H |
| 26 | $C_2H_5$ | (VI) | 4 | H | S | H | H |
| 27 | $CH_3$ | (VII) | 2 | 4,6-$Cl_2$ | O | $CH_3$ | $CH_3$ |
| 28 | $C_2H_5$ | (VII) | 4 | H | S | Cl | H |

| Compound No. | $R_1$ | $R_2$ general formula | Y | position | $(R_8)_p$ | Y | $R_9$ | $R_{10}$ |
|---|---|---|---|---|---|---|---|---|
| 29 | $C_2H_5$ | (VIII) | O | 2 | 2-Cl | O | H | H |
| 30 | $C_2H_5$ | (VIII) | S | 3 | H | S | H | H |
| 31 | $C_2H_5$ | (VIII) | S | 2 | 5-Cl | S | Cl | H |
| 32 | $C_2H_5$ | (VIII) | S | 3 | H | O | $CH_3$ | $CH_3$ |
| 33 | $C_2H_5$ | (VIII) | $NCH_3$ | 2 | H | S | H | H |
| 34 | $CH_3$ | (IX) | O | 2 | H | S | H | H |
| 35 | $C_2H_5$ | (IX) | O | 4 | H | S | Cl | H |
| 36 | $C_2H_5$ | (IX) | S | 2 | 4-$CH_3$ | S | H | H |
| 37 | $C_2H_5$ | (IX) | S | 5 | H | O | $CH_3$ | H |
| 38 | $C_2H_5$ | (X) | O | 3 | H | O | H | H |
| 39 | $C_2H_5$ | (X) | O | 5 | H | S | $CH_3$ | H |
| 40 | $C_2H_5$ | (X) | S | 4 | 3,5-$(CH_3)_2$ | O | Br | Br |
| 41 | $C_2H_5$ | (XI) | O | 2 | H | S | H | H |
| 42 | $C_2H_5$ | (XI) | S | 2 | 5-$SCH_3$ | $NCH_3$ | H | H |
| 43 | $C_2H_5$ | (XI) | $NCH_3$ | 2 | H | O | H | H |

TABLE 2

Compounds in general formula (A-2)
Substituent in general formula (A-2)

| Compound No. | R$_1$ | general formula | R$_2$ (R$_5$)$_n$ | Y | R$_9$ | R$_{10}$ |
|---|---|---|---|---|---|---|
| 44 | C$_2$H$_5$ | (II) | H | O | H | Br |
| 45 | C$_2$H$_5$ | (II) | H | O | H | Cl |
| 46 | C$_2$H$_5$ | (II) | o-F | S | H | Cl |
| 47 | n-Pr | (II) | o-F | S | H | H |
| 48 | C$_2$H$_5$ | (II) | o-Cl | S | H | H |
| 49 | C$_2$H$_5$ | (II) | o-Br | S | CH$_3$ | CH$_3$ |
| 50 | C$_2$H$_5$ | (II) | o-CH$_3$ | S | H | SCH$_3$ |
| 51 | CH$_3$ | (II) | o-CH$_3$ | O | H | OCH$_3$ |
| 52 | CH$_3$ | (II) | m-OCOCH$_3$ | S | H | H |
| 53 | CH$_3$ | (II) | p-SCH$_3$ | O | H | OAc |
| 54 | CH$_3$ | (II) | p-C(CH$_3$)$_3$ | NCH$_3$ | H | F |
| 55 | C$_2$H$_5$ | (II) | p-Cl | NCH$_3$ | H | Cl |

| Compound No. | R$_1$ | general formula | R$_2$ Y | position | (R$_8$)$_p$ | Y | R$_9$ | R$_{10}$ |
|---|---|---|---|---|---|---|---|---|
| 56 | C$_2$H$_5$ | (VIII) | O | 2 | H | S | H | F |
| 57 | C$_2$H$_5$ | (VIII) | O | 3 | 2-Cl | O | H | Cl |
| 58 | C$_2$H$_5$ | (VIII) | S | 2 | 5-Cl | O | H | Cl |
| 59 | C$_2$H$_5$ | (VIII) | S | 3 | 2-CH$_3$ | S | H | CH$_3$ |
| 60 | C$_2$H$_5$ | (VIII) | NCH$_3$ | 2 | H | S | H | H |
| 61 | CH$_3$ | (IX) | O | 2 | H | O | H | H |
| 62 | C$_2$H$_5$ | (IX) | O | 5 | 2-Cl | S | Cl | Cl |
| 63 | C$_2$H$_5$ | (IX) | S | 2 | 4-CH$_3$ | S | H | H |
| 64 | C$_2$H$_5$ | (IX) | S | 4 | H | O | CH$_3$ | CH$_3$ |
| 65 | C$_2$H$_5$ | (X) | O | 3 | H | O | H | OCF$_3$ |
| 66 | C$_2$H$_5$ | (X) | O | 4 | 5-CH$_3$ | S | CH$_3$ | CH$_3$ |
| 67 | C$_2$H$_5$ | (X) | S | 5 | H | O | Br | Br |
| 68 | CH$_3$ | (XI) | O | 2 | H | S | H | SCH$_3$ |
| 69 | C$_2$H$_5$ | (XI) | S | 2 | 5-SCH$_3$ | S | H | H |
| 70 | n-Pr | (XI) | S | 2 | 5-F | NCH$_3$ | H | H |

TABLE 3

Compounds in general formula (A-3)
Substituent in general formula (A-3)

| Compound No. | R$_1$ | general formula | R$_2$ (R$_5$)$_n$ | Y | R$_9$ | R$_{10}$ |
|---|---|---|---|---|---|---|
| 71 | CH$_3$ | (II) | H | O | H | H |
| 72 | C$_2$H$_5$ | (II) | H | S | H | H |
| 73 | n-Pr | (II) | o-F | S | H | Cl |
| 74 | n-Pr | (II) | o-F | S | H | H |
| 75 | C$_2$H$_5$ | (II) | o-Cl | S | H | CH$_3$ |
| 76 | C$_2$H$_5$ | (II) | o-F | S | H | H |
| 77 | C$_2$H$_5$ | (II) | o-CH$_3$ | S | H | H |
| 78 | C$_2$H$_5$ | (II) | o-CH$_3$ | O | H | H |
| 79 | CH$_3$ | (II) | m-OCF$_3$ | S | H | Cl |
| 80 | C$_2$H$_5$ | (II) | H | NCH$_3$ | H | H |
| 81 | CH$_3$ | (II) | o-F | NCH$_3$ | H | H |
| 82 | C$_2$H$_5$ | (II) | o-CH$_3$ | NAc | H | H |

| Compound No. | R$_1$ | general formula | R$_2$ R$_6$ | R$_7$ | (R$_8$)$_p$ | Y | R$_9$ | R$_{10}$ |
|---|---|---|---|---|---|---|---|---|
| 83 | CH$_3$ | (III) | H | CH$_3$ | p-CH$_3$ | O | H | Cl |
| 84 | C$_2$H$_5$ | (III) | H | CH$_3$ | H | S | H | H |
| 85 | C$_2$H$_5$ | (III) | H | C$_2$H$_5$ | H | NCH$_3$ | H | H |

TABLE 3-continued

Compounds in general formula (A-3)
Substituent in general formula (A-3)

| Compound No. | $R_1$ | general formula | q | r | X | $(R_8)_p$ | Y | $R_9$ | $R_{10}$ |
|---|---|---|---|---|---|---|---|---|---|
| | | | | | $R_2$ | | | | |
| 86 | $CH_3$ | (IV) | 1 | 1 | $CH_2$ | H | O | H | H |
| 87 | $C_2H_5$ | (IV) | 0 | 1 | $CH_2$ | H | O | H | $SCH_3$ |
| 88 | $C_2H_5$ | (IV) | 1 | 1 | O | H | S | H | Cl |
| 89 | $C_2H_5$ | (IV) | 1 | 1 | S | H | $NCH_3$ | H | H |

| Compound No. | $R_1$ | general formula | position | $(R_8)_p$ | Y | $R_9$ | $R_{10}$ |
|---|---|---|---|---|---|---|---|
| | | | $R_2$ | | | | |
| 90 | $C_2H_5$ | (V) | 1 | 5-Cl | O | H | H |
| 91 | $C_2H_5$ | (V) | 2 | 8-Cl | S | H | Br |
| 92 | $C_2H_5$ | (V) | 2 | H | S | H | Cl |
| 93 | $C_2H_5$ | (VI) | 2 | 5-Cl | O | H | H |
| 94 | $C_2H_5$ | (VI) | 4 | H | S | H | Cl |
| 95 | $C_2H_5$ | (VII) | 4 | H | S | Cl | H |

| Compound No. | $R_1$ | general formula | Y | position | $(R_8)_p$ | Y | $R_9$ | $R_{10}$ |
|---|---|---|---|---|---|---|---|---|
| | | | | $R_2$ | | | | |
| 96 | $C_2H_5$ | (VIII) | O | 3 | 2-Cl | O | H | H |
| 97 | $C_2H_5$ | (VIII) | O | 2 | H | O | H | H |
| 98 | $C_2H_5$ | (VIII) | S | 2 | 5-Cl | S | H | Cl |
| 99 | $C_2H_5$ | (VIII) | S | 2 | H | S | H | H |
| 100 | $C_2H_5$ | (VIII) | $NCH_3$ | 3 | H | S | H | $CH_3$ |
| 101 | $C_2H_5$ | (IX) | O | 4 | H | S | H | H |
| 102 | $CH_3$ | (IX) | S | 2 | 4-$CH_3$ | NAc | H | H |
| 103 | $C_2H_5$ | (IX) | S | 4 | H | O | $CH_3$ | $CH_3$ |
| 104 | $C_2H_5$ | (X) | O | 3 | H | NEt | H | H |
| 105 | $C_2H_5$ | (X) | S | 3 | H | S | H | F |
| 106 | $C_2H_5$ | (XI) | O | 2 | H | S | H | H |
| 107 | $C_2H_5$ | (XI) | S | 2 | 5-$CF_3$ | $NCH_3$ | H | H |
| 108 | $C_2H_5$ | (XI) | $NCH_3$ | 2 | H | O | H | H |

TABLE 4

Compounds in general formula (A-4)
Substituent in general formula (A-4)

| Compound No. | $R_1$ | general formula | $(R_5)_n$ | $R_9$ |
|---|---|---|---|---|
| | | | $R_2$ | |
| 109 | $CH_3$ | (II) | H | H |
| 110 | $C_2H_5$ | (II) | o-F | H |

| Compound No. | $R_1$ | general formula | Y | position | $(R_8)_p$ | $R_9$ |
|---|---|---|---|---|---|---|
| | | | | $R_2$ | | |
| 111 | $C_2H_5$ | (VIII) | O | 2 | H | H |
| 112 | $C_2H_5$ | (VIII) | S | 2 | H | H |
| 113 | $CH_3$ | (IX) | O | 2 | H | H |
| 114 | $C_2H_5$ | (X) | O | 2 | H | H |

TABLE 5

Compounds in general formula (A-5)
Substituent in general formula (A-5)

| Compound No. | $R_1$ | general formula | $(R_5)_n$ | Y | $R_9$ |
|---|---|---|---|---|---|
| | | | $R_2$ | | |
| 115 | $CH_3$ | (II) | H | O | H |
| 116 | $C_2H_5$ | (II) | H | S | H |
| 117 | $C_2H_5$ | (II) | o-F | S | H |
| 118 | n-Pr | (II) | 2,4-$F_2$ | S | Cl |
| 119 | $C_2H_5$ | (II) | o-Cl | O | H |
| 120 | $C_2H_5$ | (II) | o-$CH_3$ | S | Cl |
| 121 | $C_2H_5$ | (II) | o-$CH_3$ | O | $CH_3$ |
| 122 | $C_2H_5$ | (II) | 3-Cl,4-F | O | H |
| 123 | $CH_3$ | (II) | m-$CF_3$ | $NCH_3$ | H |

| Compound No. | $R_1$ | general formula | Y | position | $(R_8)_p$ | Y | $R_9$ |
|---|---|---|---|---|---|---|---|
| | | | | $R_2$ | | | |
| 124 | $C_2H_5$ | (VIII) | O | 2 | H | O | H |
| 125 | $C_2H_5$ | (VIII) | O | 3 | 2-Cl | S | Cl |
| 126 | $C_2H_5$ | (VIII) | S | 2 | 5-Cl | S | H |
| 127 | $C_2H_5$ | (VIII) | S | 3 | H | O | $CH_3$ |
| 128 | $CH_3$ | (IX) | O | 2 | H | S | H |
| 129 | $C_2H_5$ | (IX) | O | 4 | H | S | Cl |

TABLE 5-continued

Compounds in general formula (A-5)
Substituent in general formula (A-5)

| | | | | | | | |
|---|---|---|---|---|---|---|---|
| 130 | C₂H₅ | (IX) | S | 2 | 4-CH₃ | S | H |
| 131 | C₂H₅ | (X) | O | 3 | H | O | H |
| 132 | C₂H₅ | (X) | S | 5 | H | S | CH₃ |
| 133 | C₂H₅ | (XI) | O | 2 | H | S | H |
| 134 | C₂H₅ | (XI) | S | 2 | 5-SCH₃ | NCH₃ | H |

TABLE 6

Compounds in general formula (A-6)
Substituent in general formula (A-6)

| | | | R₂ | | |
|---|---|---|---|---|---|
| Compound No. | R₁ | general formula | (R₅)ₙ | Y | R₉ |
| 135 | C₂H₅ | (II) | H | O | H |
| 136 | C₂H₅ | (II) | H | S | H |
| 137 | C₂H₅ | (II) | o-F | S | H |
| 138 | C₂H₅ | (II) | o-F | NCH₃ | Cl |
| 139 | C₂H₅ | (II) | o-Cl | S | H |
| 140 | C₂H₅ | (II) | o-Br | S | H |
| 141 | C₂H₅ | (II) | o-CH₃ | S | H |
| 142 | C₂H₅ | (II) | o-CH₃ | O | H |
| 143 | C₂H₅ | (II) | p-C₂H₅ | O | H |
| 144 | CH₃ | (II) | p-OCH₃ | NCH₃ | H |

| | | | | | R₂ | | |
|---|---|---|---|---|---|---|---|
| Compound No. | R₁ | general formula | Y | position | (R₈)ₚ | Y | R₉ |
| 145 | C₂H₅ | (VIII) | O | 3 | 2-Cl | S | Cl |
| 146 | C₂H₅ | (VIII) | S | 2 | 5-Cl | S | H |
| 147 | C₂H₅ | (VIII) | S | 3 | H | O | H |
| 148 | C₂H₅ | (VIII) | NCH₃ | 2 | H | S | H |
| 149 | CH₃ | (IX) | O | 2 | H | S | H |
| 150 | C₂H₅ | (IX) | S | 2 | 4-CH₃ | S | H |
| 151 | C₂H₅ | (IX) | S | 4 | H | O | CH₃ |
| 152 | C₂H₅ | (X) | O | 3 | H | O | H |
| 153 | C₂H₅ | (X) | O | 5 | H | O | H |
| 154 | C₂H₅ | (X) | S | 5 | H | S | H |
| 155 | C₂H₅ | (XI) | O | 2 | H | S | H |
| 156 | C₂H₅ | (XI) | S | 2 | 5-SCH₃ | NCH₃ | H |
| 157 | C₂H₅ | (XI) | NCH₃ | 2 | H | O | H |

TABLE 7

Compounds in general formula (A-7)
Substituent in general formula (A-7)

| | | | R₂ | | |
|---|---|---|---|---|---|
| Compound No. | R₁ | general formula | (R₅)ₙ | Y | R₉ |
| 158 | C₂H₅ | (II) | H | S | H |
| 159 | C₂H₅ | (II) | o-F | O | H |
| 160 | C₂H₅ | (II) | o-F | S | Cl |
| 161 | C₂H₅ | (II) | o-Cl | S | H |
| 162 | C₂H₅ | (II) | o-CH₃ | S | CF₃ |
| 163 | C₂H₅ | (II) | o-CH₃ | O | CH₃ |
| 164 | CH₃ | (II) | m-OCH₃ | S | Cl |
| 165 | C₂H₅ | (II) | 2,4-(CH₃)₂ | O | H |
| 166 | CH₃ | (II) | p-OCF₃ | NCH₃ | H |
| 167 | C₂H₅ | (II) | 2,4-F₂ | NCH₃ | H |

| | | | | | R₂ | | |
|---|---|---|---|---|---|---|---|
| Compound No. | R₁ | general formula | Y | position | (R₈)ₚ | Y | R₉ |
| 168 | C₂H₅ | (VIII) | O | 2 | H | O | H |
| 169 | C₂H₅ | (VIII) | O | 3 | H | S | Cl |
| 170 | C₂H₅ | (VIII) | S | 2 | 5-Cl | S | Cl |
| 171 | C₂H₅ | (VIII) | S | 3 | H | O | CH₃ |
| 172 | C₂H₅ | (VIII) | NCH₃ | 3 | H | NCH₃ | H |
| 173 | CH₃ | (IX) | O | 2 | H | S | H |
| 174 | C₂H₅ | (IX) | S | 5 | 2-Cl | S | Cl |
| 175 | C₂H₅ | (IX) | S | 5 | 4-CH₃ | S | H |
| 176 | C₂H₅ | (IX) | S | 4 | H | O | CH₃ |
| 177 | C₂H₅ | (X) | O | 3 | H | O | H |
| 178 | C₂H₅ | (X) | O | 5 | H | S | CH₃ |
| 179 | C₂H₅ | (XI) | O | 2 | H | S | H |
| 180 | C₂H₅ | (XI) | S | 2 | 5-C₂H₅ | NEt | H |
| 181 | C₂H₅ | (XI) | NCH₃ | 2 | H | O | H |

TABLE 8

Compounds in general formula (A-8)
Substituent in general formula (A-8)

| | | | R₂ | | |
|---|---|---|---|---|---|
| Compound No. | R₁ | general formula | (R₅)ₙ | Y | R₉ |
| 182 | C₂H₅ | (II) | H | O | H |
| 183 | C₂H₅ | (II) | o-F | O | H |
| 184 | CH₃ | (II) | o-F | S | H |
| 185 | C₂H₅ | (II) | o-Cl | S | Cl |
| 186 | C₂H₅ | (II) | o-Cl | S | H |
| 187 | C₂H₅ | (II) | o-Br | S | i-Pr |
| 188 | C₂H₅ | (II) | o-CH₃ | S | CH₃ |

| | | | | | R₂ | | |
|---|---|---|---|---|---|---|---|
| Compound No. | R₁ | general formula | Y | position | (R₈)ₚ | Y | R₉ |
| 189 | C₂H₅ | (VIII) | O | 2 | H | O | H |
| 190 | C₂H₅ | (VIII) | O | 3 | 2-Cl | S | Cl |
| 191 | C₂H₅ | (VIII) | S | 2 | 5-Cl | S | H |
| 192 | C₂H₅ | (VIII) | S | 3 | H | O | CH₃ |
| 193 | C₂H₅ | (VIII) | NCH₃ | 2 | H | S | H |
| 194 | C₃ | (IX) | O | 2 | H | S | H |
| 195 | C₂H₅ | (IX) | O | 4 | 2-Cl | O | Cl |
| 196 | C₂H₅ | (IX) | S | 4 | H | S | H |
| 197 | C₂H₅ | (IX) | S | 4 | H | O | CH₃ |
| 198 | C₂H₅ | (X) | O | 3 | H | O | H |
| 199 | C₂H₅ | (X) | S | 4 | 3,5-(CH₃)₂ | O | H |
| 200 | C₂H₅ | (XI) | O | 2 | H | S | H |
| 201 | C₂H₅ | (XI) | S | 2 | 5-SCH₃ | NCH₃ | H |

TABLE 9

Physical properties of the compound in general formula (I)

| Compound No. | Physical properties [¹H-NMR(CDCl₃, 270MHz); δppm] |
|---|---|
| 2 | 0.88(3H, t, J=7.3Hz), 1.75(2H, dq, J=7.3, 7.3Hz), 4.02(1H, d, J=2.9Hz), 4.16–4.23(1H, m), 4.25(1H, d, J=2.9Hz), 4.55(1H, d, J=11.7Hz), 4.59(1H, d, J=13.9Hz), 4.75(1H, d, J=11.7Hz), 4.83(1H, d, J=13.9Hz), 5.02(1H, d, J=2.9Hz), 6.40(1H, d, J=1.8Hz), 7.15–7.42(5H, m) |
| 4 | 0.86(3H, t, J=7.3Hz), 1.73(2H, dq, J=7.3, 7.3Hz), |

TABLE 9-continued

Physical properties of the compound in general formula (I)

| Compound No. | Physical properties [$^1$H-NMR(CDCl$_3$, 270MHz); δppm] |
|---|---|
|  | 3.99(1H, d, J=2.9Hz), 4.16–4.21(1H, m), 4.27(1H, d, J=2.9Hz), 4.47(1H, d, J=14.7Hz), 4.54(1H, d, J=11.7Hz), 4.69(1H, d, J=14.7Hz), 4.73(1H, d, J=11.7Hz), 4.86(1H, d, J=2.9Hz), 6.62(1H, s), 7.15–7.37(4H, m) |
| 5 | 0.86(3H, t, J=7.3Hz), 1.73(2H, dq, J=7.3, 7.3Hz), 2.35(3H, s), 3.99(1H, d, J=2.9Hz), 4.15–4.21(1H, m), 4.27(1H, d, J=2.9Hz), 4.47(1H, d, J=14.7Hz), 4.54(1H, d, J=11.7Hz), 4.68(1H, d, J=14.7Hz), 4.73(1H, d, J=11.7Hz), 4.86(1H, d, J=2.9Hz), 6.61(1H, s), 7.15–7.36(4H, m) |
| 6 | 0.86(3H, t, J=7.3Hz), 1.73(2H, dq, J=7.3, 7.3Hz), 2.35(3H, s), 3.99(1H, d, J=2.9Hz), 4.14–4.20(1H, m), 4.26(1H, d, J=2.9Hz), 4.49(1H, d, J=14.7Hz), 4.54(1H, d, J=11.7Hz), 4.71(1H, d, J=14.7Hz), 4.73(1H, d, J=11.7Hz), 4.87(1H, d, J=2.9Hz), 6.74(1H, s), 7.15–7.36(4H, m) |
| 77 | 0.86(3H, t, J=7.3Hz), 1.73(2H, dq, J=7.3, 7.3Hz), 2.36(3H, s), 4.01(1H, d, J=3.7Hz), 4.11–4.16(1H, m), 4.26(1H, d, J=2.9Hz), 4.56(1H, d, J=11.7Hz), 4.70(1H, d, J=14.7Hz), 4.75(1H, d, J=11.7Hz), 4.91(1H, d, J=14.1Hz), 4.89(1H, d, J=2.9Hz), 7.13–7.24(5H, m), 7.35–7.38(1H, m) |
| 97 | 0.85(3H, t, J=7.3Hz), 1.75(2H, dq, J=7.3, 7.3Hz), 4.05(1H, d, J=2.9Hz), 4.13–4.18(1H, m), 4.34(1H, d, J=2.9Hz), 4.53(1H, d, J=12.7Hz), 4.57(1H, d, J=14.7Hz), 4.68(1H, d, J=12.7Hz), 4.83(1H, d, J=14.7Hz), 4.89(1H, d, J=2.9Hz), 6.37–7.42(5H, m) |
| 99 | 0.90 (3H, t, J=7.3Hz), 1.77(2H, dq, J=7.3, 7.3Hz), 4.03(1H, d, J=3.7Hz), 4.13–4.18(1H, m), 4.29(1H, d, J=2.9Hz), 4.53(1H, d, J=11.7Hz), 4.59(1H, d, J=13.9Hz), 4.75(1H, d, J=11.7Hz), 4.83(1H, d, J=13.9Hz), 4.90(1H, d, J=2.9Hz), 6.91–7.40(5H, m) |
| 120 | 0.89(3H, t, J=7.3Hz), 1.76(2H, dq, J=7.3, 7.3Hz), 2.36(3H, s), 4.05(1H, d, J=3.7Hz), 4.13–4.18(1H, m), 4.39(1H, d, J=2.9Hz), 4.53(1H, d, J=11.7Hz), 4.58(1H, d, J=14.7Hz), 4.74(1H, d, J=11.7Hz), 4.82(1H, d, J=14.7Hz), 4.90(1H, d, J=2.9Hz), 7.13–7.41(4H, m) |
| 137 | 0.88(3H, t, J=7.3Hz), 1.75(2H, dq, J=7.3, 7.3Hz), 4.05(1H, d, J=2.9Hz), 4.13–4.17(1H, m), 4.33(1H, d, J=2.9Hz), 4.52(1H, d, J=11.7Hz), 4.58(1H, d, J=14.7Hz), 4.75(1H, d, J=11.7Hz), 4.81(1H, d, J=14.7Hz), 4.91(1H, d, J=2.9Hz), 7.05–7.44(5H, m) |
| 146 | 0.90(3H, t, J=7.3Hz), 1.74(2H, dq, J=7.3, 7.3Hz), 4.05(1H, d, J=2.9Hz), 4.12–4.18(1H, m), 4.38(1H, d, J=3.7Hz), 4.50(1H, d, J=12.4Hz), 4.57(1H, d, J=15.4Hz), 4.77(1H, d, J=12.4Hz), 4.81(1H, d, J=15.4Hz), 4.90(1H, d, J=3.7Hz), 7.15(1H, s), 7.30(1H, s) |
| 185 | 0.89(3H, t, J=7.3Hz), 1.76(2H, dq, J=7.3, 7.3Hz), 4.05(1H, d, J=2.9Hz), 4.12–4.16(1H, m), 4.35(1H, d, J=3.7Hz), 4.51(1H, d, J=11.7Hz), 4.57(1H, d, J=14.7Hz), 4.76(1H, d, J=11.7Hz), 4.83(1H, d, J=14.7Hz), 4.91(1H, d, J=3.7Hz), 7.11–7.41(4H, m) |
| 188 | 0.87(3H, t, J=7.3Hz), 1.75(2H, dq, J=7.3, 7.3Hz), 2.36(3H, s), 2.69(3H, s), 4.02(1H, d, J=2.9Hz), 4.16–4.28(2H, m), 4.55–4.95(5H, m), 7.14–7.30(4H, m) |

Formulation Examples and Test Examples

Formulation Examples for herbicides of the present invention and Test Examples for herbicidal activity of the formulations are given as follows:

Formulation Example 1: (Wettable powder)

20 Parts by weight of the compound (2) of the present invention, 2 parts by weight of Neopelex (a trade name; Kao Corporation; sodium dodecylbenzene sulfonate), 1 part by weight of Noigen EA80 ( a trade name; Daiichi Kogyo Seiyaku, polyoxyethylenenonylphenyl ether), 10 parts by weight of white carbon and 67 parts by weight of diatomaceous earth were thoroughly mashed and blended to prepare a wettable powder.

Formulation Example 2: (Wettable powder)

20 Parts by weight of the compound (3) of the present invention, 2 parts by weight of sodium alkylbenzene sulfonate, 1 part by weight of polyoxyethylenealkylphenyl ether, 10 parts by weight of white carbon and 67 parts by weight of ziegrite were thoroughly mashed and blended to prepare a wettable powder.

Formulation Example 3: (Wettable powder)

50 Parts by weight of the compound (7) of the present invention, 30 parts by weight of white carbon, 6 parts by weight of polyoxyethylenealkylphenyl ether ammonium sulfate, 2 parts by weight of lignin sodium sulfonate and 12 parts by weight of diatomaceous earth were thoroughly mashed and blended to prepare a wettable powder.

Formulation Example 4: (Flowable agent)

5 Parts by weight of the compound (8) of the present invention, 2 parts by weight of lignin sodium sulfonate and 1 part by weight of polyoxyethylenealkylaryl ether were mixed and mashed with 91.7 parts by weight of water into a fine powder using a sand grinder to prepare a flowable agent with the addition of 0.3 part by weight of Kelzan S (a trade name; Kelco; xanthan gum).

Formulation Example 5: (Flowable agent)

30 Parts by weight of the compound (30) of the present invention and 10 parts by weight of San Ekisu P252 (a trade name; Sanyo-Kokusaku Pulp; lignin sodium sulfonate;) dissolved in 50 parts by weight of water were mashed and mixed and then 0.2 part by weight of Kelzan S (a trade name; mentioned before) and 0.2 part by weight of Deltop (a trade name; Takeda Chem. Ind.; an organic iodine antifungal agent) dissolved in 9.6 parts by weight of water were added therein and mixed to prepare a flowable agent.

Formulation Example 6: (Powder)

1 Part by weight of the compound (76) of the present invention, 0.5 part by weight of Emulgen 910 (a trade name; Kao Corporation; polyoxyethylenenonylphenyl ether) and 98.5 parts by weight of kaolin clay were thoroughly mashed and mixed to obtain a powder.

Formulation Example 7: (Powder)

3 Parts by weight of the compound (78) of the present invention, 3 parts by weight of lignin sodium sulfonate, 2 parts by weight polyoxyethylenealkylaryl ether and 92 parts by weight of clay were mashed and mixed to obtain a powder.

Formulation Example 8: (Water dispersible granules)

55 Parts by weight of the compound (97) of the present invention, 5 parts by weight of Toxanon 60PN (a trade name; Sanyo Kasei Kogyo; polymer anion), 5 parts by weight of polyoxyethylenealkylaryl ether and 35 parts by weight of white carbon were thoroughly mixed and then the mixture was moistened with an appropriate amount of water and then compressed to granules using a side-extrusion granulator. The resultant granules were dried at 30–60° C., broken up and then finely granulated to a diameter of 0.3–0.5 mm using a refiner to obtain water dispersible granules.

Formulation Example 9: (Granules)

3 Parts by weight of the compound (99) of the present invention, 2 parts by weight of Neopelex (a trade name; mentioned before), 2 parts by weight of San Ekisu P252 (a trade name; mentioned before), 70 parts by weight of bentonite and 23 parts by weight of talc were thoroughly mixed and moistened with an appropriate amount of water and the mixture was then granulated using a side-extrusion granulator. The resultant granules were dried in air at 30–60° C., broken up and then finely granulated using a refiner to a diameter of 0.3–1 mm to obtain a granules.

Formulation Example 10: (Granules)

0.5 Part by weight of the compound (120) of the present invention, 2 parts by weight of Gosenol GL-05s (a trade name of Nippon Gosei Kagaku; PVA), 2 parts by weight of San Ekisu P252 (a trade name; mentioned before) and 95.5 parts by weight of clay were thoroughly mixed and moistened with an appropriate amount of water. The mixture was then granulated using a side-extrusion granulator. The resultant granules were dried in air at 60–90° C., broken up and then finely granulated using a refiner to a diameter of 0.3–1 mm to obtain a granules.

Formulation Example 11: (Emulsion)

10 Parts by weight of the compound (137) of the present invention, 10 parts by weight of Sorpol 800A (a trade name; Toho Pharmaceutical Inc.; a mixture of nonionic surfactant and anion surfactant) and 80 parts by weight of o-xylene were mixed and dissolved to obtain an emulsion.

Formulation Example 12: (Wettable powder)

20 Parts by weight of the compound (146) of the present invention, 2 parts by weight of sodium alkylbenzene sulfonate, 1 part by weight of polyoxyethylenealkylphenyl ether, 15 parts by weight of white carbon and 62 parts by weight of ziegrite were thoroughly mashed and blended to prepare a wettable powder.

Formulation Example 13: (Wettable powder)

50 Parts by weight of the compound (185) of the present invention, 30 parts by weight of white carbon, 6 parts by weight of polyoxyethylenealkylphenyl ether ammonium sulfate, 2 parts by weight of lignin sodium sulfonate and 12 parts by weight of diatomaceous earth were thoroughly mashed and blended to prepare a wettable powder.

Formulation Example 14: (Oil-in-water type emulsion EW)

5 Parts by weight of the compound (3) of the present invention, 4 parts by weight of Toxanon FW-10 (a trade name; mentioned before), 0.3 part by weight of Kelzan S(a trade name; mentioned before), 0.2 part by weight of Deltop (a trade name; Takeda Pharmaceutical Inc.; organic iodine antifungal agent) and 2 parts by weight of polyoxyethylene-alkylaryl ether were emulsified with 88.5 parts by weight of water by a homo-mixer to obtain an oil-in-water type emulsion EW.

Formulation Example 15: (Oil-in-water type emulsion EW)

30 Parts by weight of the compound (2) of the present invention, 4 parts by weight of Gosenol KH-20 (a trade name; mentioned before), 0.3 part by weight of kelzen S (a trade name mentioned above), 0.2 part by weight of Deltop (above noted) and 4 parts by weight of polyoxyethylene-alkylaryl ether were mashed and mixed with 61.5 parts by weight of water to obtain an oil-in-water type emulsion EW.

Formulation Example 16: (Water dispersible granules)

50 Parts by weight of the compound (7) of the present invention, 5 parts by weight of Toxanon 60PN (a trade name; mentioned before), 5 parts by weight of polyoxyethylene-alkylaryl ether and 40 parts by weight of white carbon were thoroughly mixed and then the mixture was moistened with an appropriate amount of water and then compressed to granules using a side-extrusion granulator. The resultant granules were dried at 30–60° C., broken up and then finely granulated to a diameter of 0.3–0.5 mm using a refiner to obtain water dispersible granules.

Formulation Example 17: (Granules)

3 Parts by weight of the compound (8) of the present invention, 2 parts by weight of Neopelex (a trade name; mentioned before), 2 parts by weight of San Ekisu P252 (a trade name; mentioned before), 70 parts by weight of bentonite and 23 parts by weight of talc were thoroughly mixed and moistened with an appropriate amount of water and the mixture was then granulated using a side-extrusion granulator. The resultant granules were dried in air at 30–60° C., broken up and then finely granulated using a refiner to a diameter of 0.3–1 mm to obtain granules.

Formulation Example 18: (Granules)

1 Part by weight of the compound (30) of the present invention, 2 parts by weight of Gosenol GL-05s (a trade name; mentioned before), 2 parts by weight of San Ekisu P252 (a trade name mentioned before) and 95 parts by weight of clay were thoroughly mixed and moistened with an appropriate amount of water and the mixture was then granulated using a side-extrusion granulator. The resultant granules were dried in air at 60–90° C., broken up and then finely granulated using a refiner to a diameter of 0.3–1 mm to obtain a granules.

Test Example 1: Flooding soil treatment test (with water seeping; before onset of weed growth)

1/5000-are Wagner pots were filled with soil, seeded with *Echinochloa oryzicola, Monochoria vaginalis, Scirpus juncoides* and *Lindernia pyxidaria* and then flooded with water. Two plants of paddy rice (with 2–3 leaves, two seedlings per plant) were transplanted to these pots and were grown in a green house. One day after the transplant (before onset of weed growth), the pots were treated with granules (which were prepared according to the method described in the above-mentioned Formulation Example 9), containing test compounds of 2 kg/ha. The water level above the soil line was maintained at 3 cm. Starting from the day after treatment, water was drained from the pot through a glass tube inserted in the bottom. The drip rate was set so that the water level was reduced by 1 cm/day, and continued for 10 days. Thirty days after the treatment, the degree of weed control and damage by the chemicals on the rice plants were investigated. Results are shown in Table 10.

In the Table, the degree of weed control and damage by herbicides on crop plants are denoted as follows by comparing the growth rates of treated plants with those of corresponding untreated plants (growth rate is expressed as a ratio (percent) of the air dry weight of treated plant to that of untreated plant).

| Degree | Growth rate (%) | Extent of damage |
|---|---|---|
| 5 | 0–5 | Dead |
| 4 | 6–10 | Extensive |
| 3 | 11–40 | Medium |
| 2 | 41–70 | Little |
| 1 | 71–90 | Slight |
| 0 | 91–100 | None |

TABLE 10

Results of flooding soil treatment test
(under seepage, pre-emergence of weeds)

| Compound | EO | MV | SJ | LP | Paddy rice |
|---|---|---|---|---|---|
| 3 | 5 | 5 | 5 | 5 | 0 |
| 7 | 5 | 5 | 5 | 5 | 0 |
| 8 | 5 | 5 | 5 | 5 | 0 |
| 30 | 5 | 5 | 5 | 5 | 0 |
| 78 | 5 | 5 | 5 | 5 | 0 |
| 99 | 5 | 5 | 5 | 5 | 0 |
| (XVII) | 5 | 5 | 5 | 5 | 2 |
| (XVIII) | 5 | 4 | 4 | 4 | 1 |

EO = *Echinochloa orizicola*
SJ = *Scirpus juncoides*
MV = *Monochoria vaginalis*
LP = *Lindernia pyxidaria*

Control agent: A compound described in Japanese Patent Laid-open No. 316579/1994

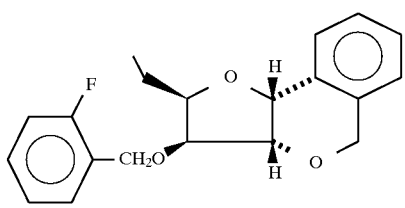

(XVII)

Control agent: A compound described in Japanese Patent Laid-open No. 138260/1995

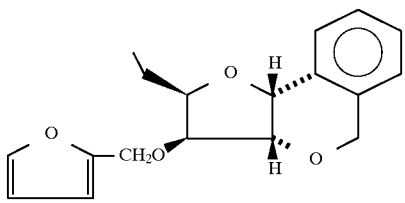

(XVIII)

Test Example 2: Flooding soil treatment test (with water seeping; post emergence of weeds)

1/5000—are Wagner pots were filled with soil, seeded with *Echinochloa oryzicola, Monochoria vaginalis, Scirpus juncoides* and *Lindernia pyxidaria* and then flooded with water. Two plants of paddy rice (with 2–3 leaves, two seedlings per plant) were transplanted to these pots and were grown in a green house. At the 2nd leaf stage of *Echinochloa oryzicola*, the pots were treated with granules (which were prepared according to the method described in the above-mentioned Formulation Example 9), containing test compounds of 2 kg/ha. The water level above the soil line was maintained at 3 cm. Starting from the day after treatment, water was drained from the pot through a glass tube inserted in the bottom. The drip rate was set so that the water level was reduced by 1 cm/day, and continued for 10 days. Thirty days after the treatment, the degree of weed control and damage by the chemicals on the rice plants were investigated. Results are shown in Table 11.

In the Table, the degree of weed control and damage by herbicides on crop plants are denoted in the same manner as described in Test Example 1.

TABLE 11

Results of flooding soil treatment test
(under seepage, growing stage of weeds)

| Compound No. | EO | MV | SJ | LP | Paddy rice |
|---|---|---|---|---|---|
| 2 | 5 | 5 | 5 | 5 | 0 |
| 3 | 5 | 5 | 5 | 5 | 0 |
| 7 | 5 | 5 | 5 | 5 | 0 |
| 8 | 5 | 5 | 5 | 5 | 0 |
| 17 | 5 | 5 | 5 | 5 | 0 |
| 30 | 5 | 5 | 5 | 5 | 0 |
| 46 | 5 | 5 | 5 | 5 | 0 |
| 76 | 5 | 5 | 5 | 5 | 0 |
| 78 | 5 | 5 | 5 | 5 | 0 |
| 84 | 5 | 5 | 5 | 5 | 0 |
| 97 | 5 | 5 | 5 | 5 | 0 |
| 99 | 5 | 5 | 5 | 5 | 0 |
| 109 | 5 | 5 | 5 | 5 | 0 |
| 120 | 5 | 5 | 5 | 5 | 0 |
| 137 | 5 | 5 | 5 | 5 | 0 |
| 146 | 5 | 5 | 5 | 5 | 0 |
| 185 | 5 | 5 | 5 | 5 | 0 |

TABLE 11-continued

Results of flooding soil treatment test
(under seepage, growing stage of weeds)

| Compound No. | EO | MV | SJ | LP | Paddy rice |
|---|---|---|---|---|---|
| (XVII) | 5 | 5 | 5 | 5 | 1 |
| (XVIII) | 5 | 4 | 3 | 4 | 1 |

Control agents: Refer under notes of Table 10

Test Example 3: Upland soil treatment test (before onset of weed growth)

1/2500—are resin pots were filled with soil, covered with soil mixed with seeds of *Echinochloa sp., Digitaria adscendeus, Setaria viridis, Stellaria media, Amaranthus retroflexus*, soybean and cotton to a depth of 1–2 cm and then placed in a green house. One day after seeding (before onset of weed growth), specified amounts of the wettable powders (which were prepared according to the method described in the above-mentioned Formulation Example 1), which were diluted with water to contain test compounds at a concentration of 3 kg/ha, were evenly sprayed over the head of plants using a pressure microspray in an amount corresponding to 10 liters/are. Thirty days after spraying, the degree of weed control and damage by the chemicals on the crops were investigated. Results are shown in Table 12. In the Table, the degree of weed control and damage by herbicides on crop plants are denoted in the same manner as described in Test Example 1.

TABLE 12

Results of Upland soil treatment test
(pre-emergence of weeds)

| Compound No. | E. sp. | DA | SV | SM | AR | Soy-beans | Cotton |
|---|---|---|---|---|---|---|---|
| 2 | 5 | 5 | 5 | 5 | 5 | 0 | 0 |
| 3 | 5 | 5 | 5 | 5 | 5 | 0 | 0 |
| 7 | 5 | 5 | 5 | 5 | 5 | 0 | 0 |
| 8 | 5 | 5 | 5 | 5 | 5 | 0 | 0 |
| 30 | 5 | 5 | 5 | 5 | 5 | 0 | 0 |
| 76 | 5 | 5 | 5 | 5 | 5 | 0 | 0 |
| 78 | 5 | 5 | 5 | 5 | 5 | 0 | 0 |
| 97 | 5 | 5 | 5 | 5 | 5 | 0 | 0 |

*E. sp. = Echinochloa sp.*
*SV = Setaria viridis*
*AR = Amaranthus retrofexus*
*DA = Diquitaria adscendeus*
*SM = Stellaria medis*

Test Example 4: Foliar application on upland plants (after onset of weed growth)

1/10000—are resin pots were filled with soil, seeded with *Echinochloa sp., Digitaria adscendeus, Setaria viridis, Stellaria media, Amaranthus retroflexus*, soybean and cotton to a depth of 1–2 cm and then placed in a green house. When 2–3 leaves of each plant appeared, calculated amounts of the wettable powders (which were prepared according to the method described in the above-mentioned Formulation Example 2), which were diluted with water to contain test compounds at a concentration of 3 kg/ha, were evenly sprayed on the surface of the soil using a pressure microspray in an amount corresponding to 10 liters/are. Thirty days after spraying, the degree of weed control and damage by the chemicals on the crops were investigated. Results are shown in Table 13. In the Table, the degree of weed control and damage by herbicides on crop plants are denoted in the same manner as described in Test Example 1.

TABLE 13

Results of foliar application on upland plants (growing stage of weeds)

| Compound No. | E. sp. | DA | SV | SM | AR | Soybeans | Cotton |
|---|---|---|---|---|---|---|---|
| 2 | 5 | 5 | 5 | 5 | 5 | 0 | 0 |
| 3 | 5 | 5 | 5 | 5 | 5 | 0 | 0 |
| 7 | 5 | 5 | 5 | 5 | 5 | 0 | 0 |
| 8 | 5 | 5 | 5 | 5 | 5 | 0 | 0 |
| 30 | 5 | 5 | 5 | 5 | 5 | 0 | 0 |
| 76 | 5 | 5 | 5 | 5 | 5 | 0 | 0 |
| 78 | 5 | 5 | 5 | 5 | 5 | 0 | 0 |

E. sp. = Echinochloa sp.
SV = Setaria viridis
AR = Amaranthus retrofexus
DA = Diquitaria adscendeus
SM = Stellaria medis The compounds of the general formula (I) according to the present invention are novel compounds exhibiting high herbicidal activity and selectivity. Namely, if used in a rice paddy, the compounds of the present invention present sufficient selectivity to the rice plants and have a high herbicidal effect on major weeds such as *Echinochloa oryzicola, Monochoria vaginalis, Scirpus juncoides* and *Lindernia pyxidaria*. Furthermore, if used in an upland field, the compounds of the present invention present sufficient selectivity to crops such as soy beans and cotton and show high herbicidal activity on major weeds such as *Echinochloa sp., Digitaria adscendeus, Setaria viridis, Stellaria media* and *Amaranthus retroflexus*. Accordingly, the compounds of the present invention can be used for herbicides which can be effectively used in rice paddy and upland field.

What is claimed is:

1. Ether compounds of the formula (I)

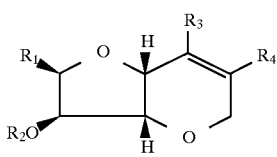
(I)

in which $R_1$ is a lower alkyl group and $R_2$ is a group selected from formulae (II)–(XI)

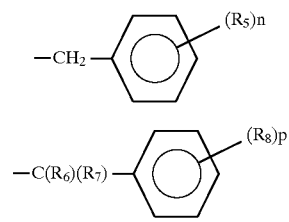
(II)
(III)

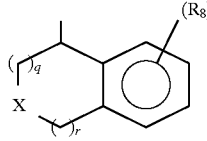
(IV)

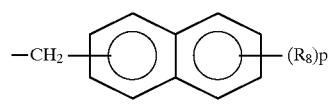
(V)

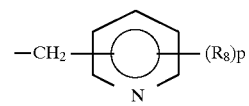
(VI)

(VII)

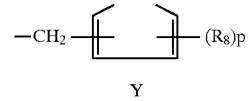
(VIII)

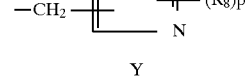
(IX)

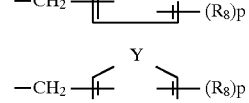
(X)

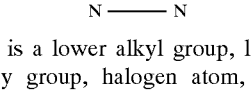
(XI)

(in which $R_5$ is a lower alkyl group, lower alkoxy group, lower acyloxy group, halogen atom, lower alkyl group substituted by a halogen atom, lower alkoxy group substituted by a halogen atom or lower alkylthio group, $R_6$ is a hydrogen atom or lower alkyl group, $R_7$ is a lower alkyl group, $R_8$ is a lower alkyl group, lower alkoxy group, lower acyloxy group, lower alkylthio group, halogen atom, lower alkyl group substituted by a halogen atom or lower alkoxy group substituted by a halogen atom, X is a methylene group, oxygen atom, sulfur atom, or nitrogen atom (which may be substituted by a lower alkyl group or lower acyl group) or may form a double bond with an adjacent carbon atom, Y is an oxygen atom, sulfur atom or nitrogen atom (which may be substituted by a lower alkyl group or lower acyl group), n is any integer between 0 and 5, p is any integer between 0 and 3, each $R_5$ and $R_8$ may be the same or different when n and p are 2 or more, q is 0 or 1, r is any integer between 0 and 2, the sum of q and r is 0, 1 or 2 and X is a methylene group when both r and q are 0) $R_3$ and $R_4$ together form an unsaturated five- or six-membered ring containing 1 or 2 hetero atoms (which may be substituted by a lower alkyl group, lower alkoxy group, lower acyloxy group, lower alkylthio group, halogen atom, lower alkyl group substituted by a halogen atom or lower alkoxy group substituted by a halogen atom).

2. Compounds in claim 1, in which $R_2$ is a group of formula (II) or (VIII)–(X), $R_3$ and $R_4$ together form an unsaturated five-membered ring having 1 or 2 hetero atoms in the ring (which may be substituted by a lower alkyl group, lower alkoxy group, lower acyloxy group, lower alkylthio group, halogen atom, lower alkyl group substituted by a halogen atom or lower alkoxy group substituted by a halogen atom).

3. Compounds in claim 1, in which $R_3$ and $R_4$ together form an unsaturated five-membered hetero ring having 1 or more oxygen atoms in the ring (which may be substituted by a lower alkyl group, lower alkoxy group, halogen atom or lower alkyl group substituted by a halogen atom).

4. Compounds in claim 1, in which $R_3$ and $R_4$ together form an unsaturated five-membered hetero ring having 1 or more sulfur atoms in the ring (which may be substituted by a lower alkyl group, lower alkoxy group, halogen atom or lower alkyl group substituted by a halogen atom).

5. A herbicide containing an ether compound of the formula (I) in claim 1 as an effective compound.

* * * * *